United States Patent
Murphy et al.

(10) Patent No.: US 9,809,627 B2
(45) Date of Patent: Nov. 7, 2017

(54) CYCLIZED TRANSTHYRETIN PEPTIDE AND METHODS OF USE THEREFOR

(71) Applicant: Wisconsin Alumni Research Foundation, Madison, WI (US)

(72) Inventors: Regina M. Murphy, Madison, WI (US); Patricia Y. Cho, Madison, WI (US); Jeffrey A. Johnson, Verona, WI (US); Xiaomeng Lu, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/884,205

(22) Filed: Oct. 15, 2015

(65) Prior Publication Data
US 2016/0108093 A1 Apr. 21, 2016

Related U.S. Application Data

(60) Provisional application No. 62/064,279, filed on Oct. 15, 2014.

(51) Int. Cl.
*C07K 14/00* (2006.01)
*C07K 7/64* (2006.01)
*A61K 38/00* (2006.01)

(52) U.S. Cl.
CPC .............. *C07K 14/001* (2013.01); *C07K 7/64* (2013.01); *A61K 38/00* (2013.01)

(58) Field of Classification Search
None
See application file for complete search history.

(56) References Cited

PUBLICATIONS

Lu et al. TANGO-Inspired Design of Anti-Amyloid Cyclic Peptides, Jun. 27, 2016, ACS Chem. Neurosci. 7:1264-1274.*

Brouillette et al., "Neurotoxicity and memory deficits induced by soluble low-molecular-weight amyloid-$\beta_{1-42}$ oligomers are revealed in vivo by using a novel animal model," *J Neurosci.*, 32(23):7852-7861, 2012.
Chen et al., "Effects of transthyretin on thyroxine and β-amyloid removal from cerebrospinal fluid in mice," *Clinical and Experimental Pharmacology and Physiology*, 43:844-850, 2016.
Endres et al., "Transnasal delivery of human A-beta peptides elicits impaired learning and memory performance in wild type mice," *BMC Neuroscience*, 17:44, 2016.
Rangasamy et al., "Intranasal delivery of NEMO-binding domain peptide prevents memory loss in a mouse model of Alzheimer's disease," *J Alzheimers Dis.*, 47(2):385-402, 2015.
Shaw, "Cystatin peptide prevents Alzheimer's pathology in CRND8 AD mice," *The FASEB Journal*, 30(1): Supplement 561.1, 2016.
Buxbaum et al., "Transthyretin protects Alzheimer's mice from the behavioral and biochemical effects of Abeta toxicity," *Proc. Natl. Acad. Sci. U. S. A.*, 105:2681-2686, 2008.
Cho et al., "A Cyclic Peptide Mimic of the β-Amyloid Binding Domain on Transthyretin," *ACS Chem. Neurosci.*, 6(5):778-789, 2015.
Cho et al., "Transthyretin-derived peptides as β-amyloid inhibitors," *ACS Chem. Neurosci.*, 5(7):542-551, 2014.
Du and Murphy, "Characterization of the interaction of β-amyloid with transthyretin monomers and tetramers," *Biochemistry*, 49(38):8276-8289, 2010.
Du et al., "Identification of beta-amyloid-binding sites on transthyretin," *Protein Eng. Des. Sel.*, 25(7):337-345, 2012.
Stein and Johnson, "Lack of neurodegeneration in transgenic mice overexpressing mutant amyloid precursor protein is associated with increased levels of transthyretin and the activation of cell survival pathways," *J. Neurosci.*, 22:7380-7388, 2002.
Stein et al.,"Neutralization of transthyretin reverses the neuroprotective effects of secreted amyloid precursor protein (APP) in APPSW mice resulting in tau phosphorylation and loss of hippocampal neurons: support for the amyloid hypothesis," *J. Neurosci.*, 24:7707-7717, 2004.
Yang, et al.,"Transthyretin as both a sensor and a scavenger of β-amyloid oligomers," *Biochemistry*, 52:2849-2861, 2013.

\* cited by examiner

*Primary Examiner* — John Ulm
(74) *Attorney, Agent, or Firm* — Parker Highlander PLLC

(57) ABSTRACT

The present disclosure describes cyclized peptides that inhibit Aβ toxicity and therefore can be used as therapeutic agents to treat Alzheimer's Disease.

25 Claims, 9 Drawing Sheets
(4 of 9 Drawing Sheet(s) Filed in Color)

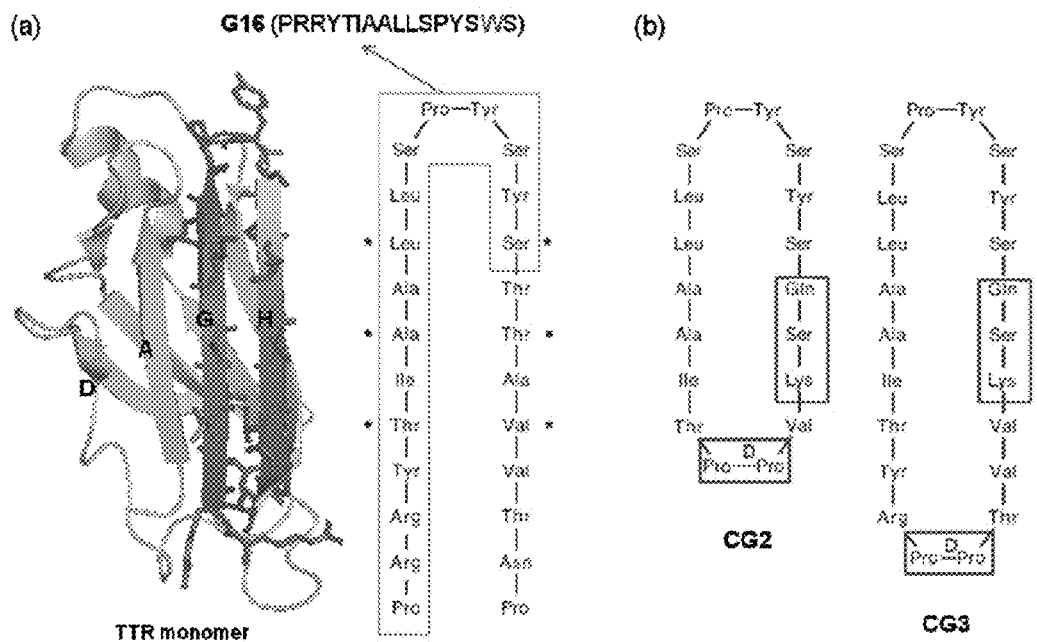
FIGS. 1A-B
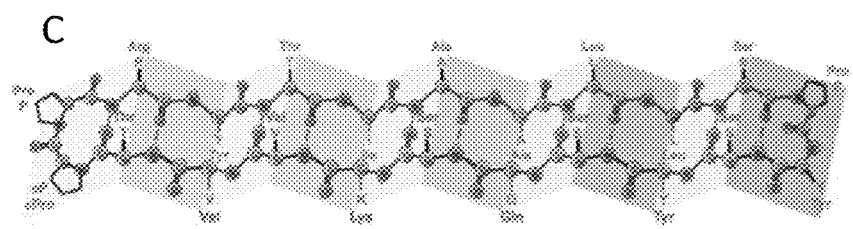
FIG. 1C

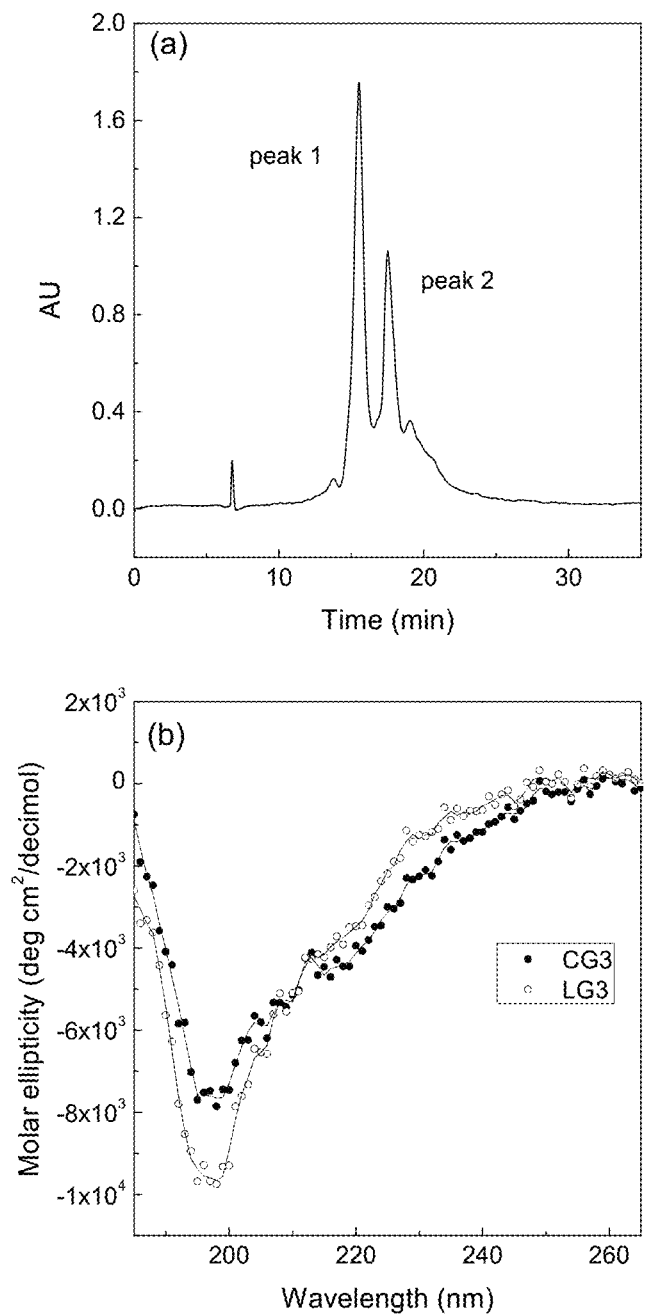
FIGS. 2A-B

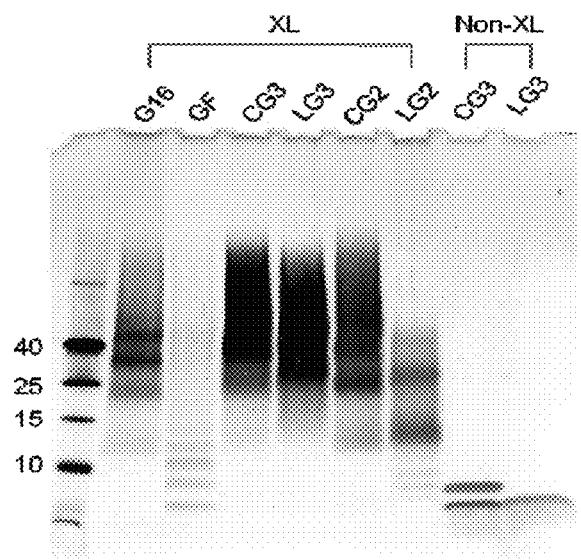
FIG. 3
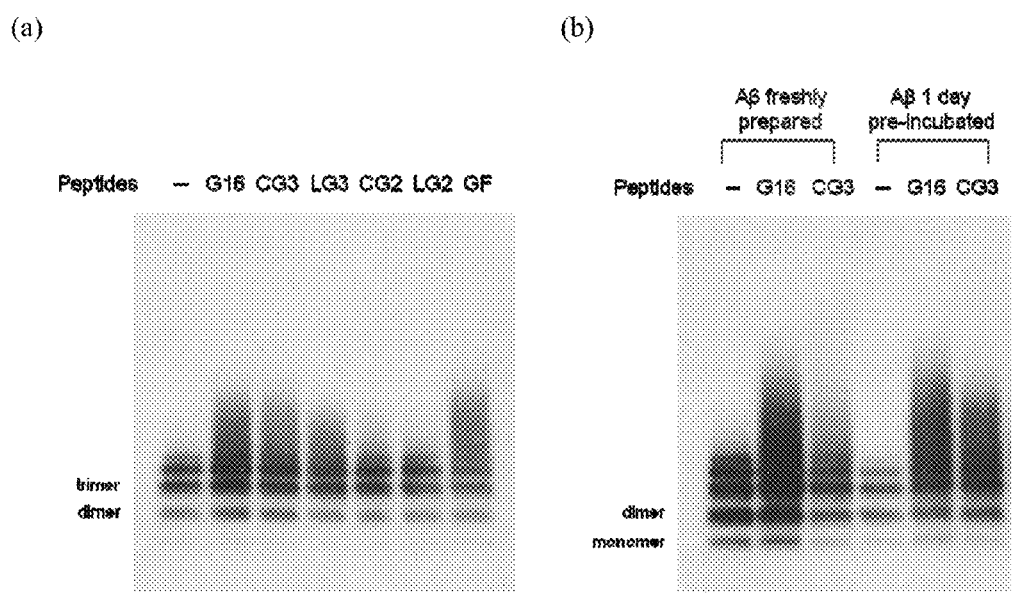
FIGS. 4A-B

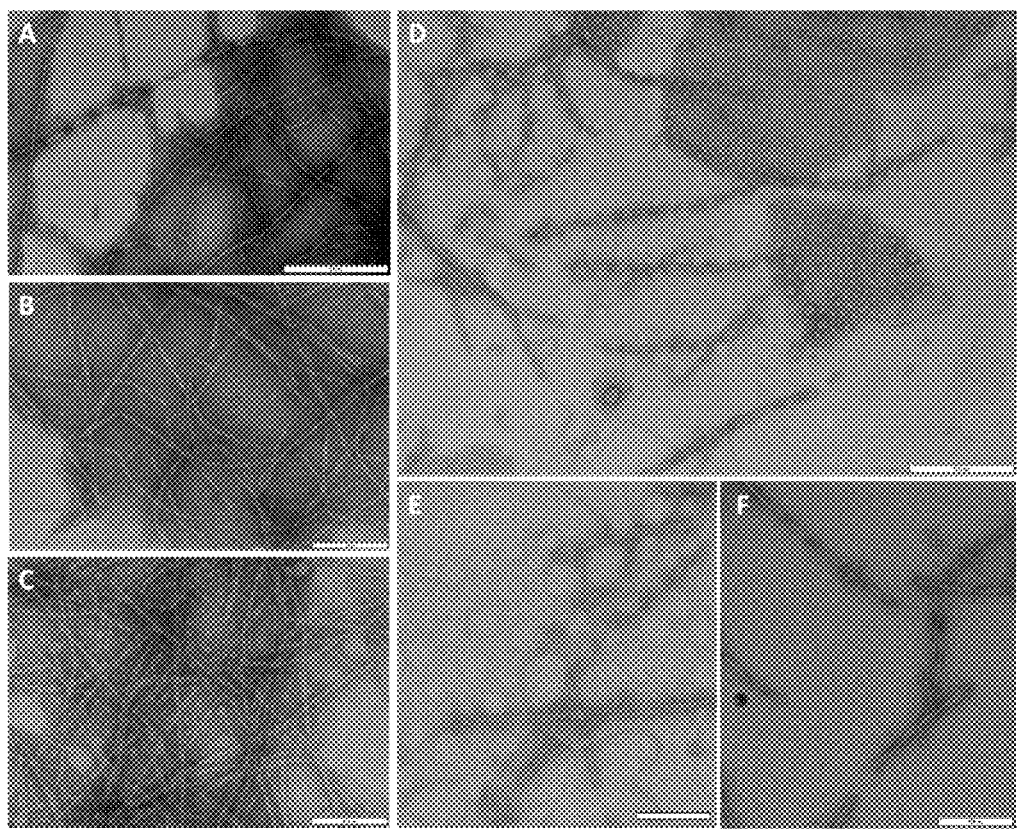
FIGS. 9A-F

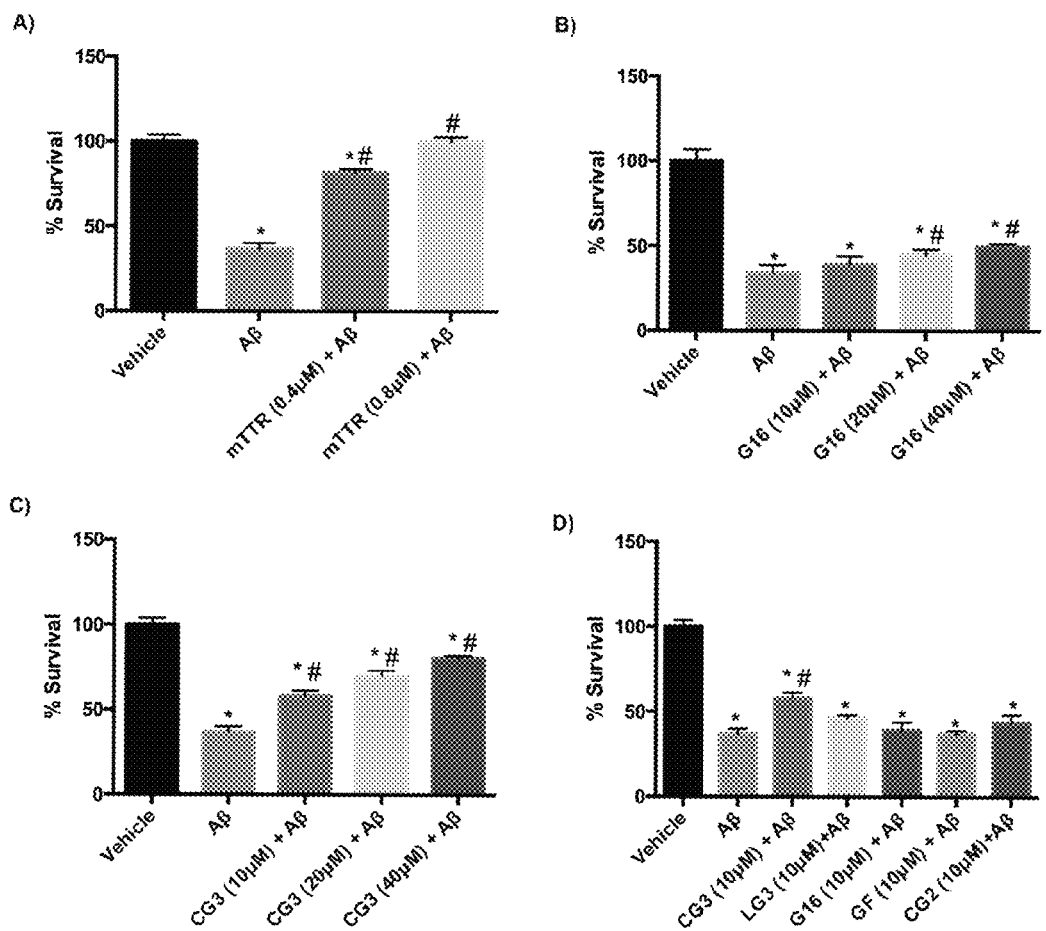
FIGS. 10A-D

__US 9,809,627 B2__

CYCLIZED TRANSTHYRETIN PEPTIDE AND METHODS OF USE THEREFOR

This application claims benefit of priority to U.S. Provisional Application Ser. No. 62/064,279, filed Oct. 14, 2014, the entire contents of which are hereby incorporated by reference.

This invention was made with government support under AG033493 awarded by the National Institutes of Health. The government has certain rights in the invention.

BACKGROUND OF THE INVENTION

1. Field of the Invention

The present disclosure relates generally to the fields of biology, medicine and pathology. More particularly, it concerns the identification and production of cyclized peptides that can protect neurons fron Aβ toxicity.

2. Description of Related Art

Alzheimer's disease (AD) is the most common form of dementia, affecting more then 35 million people worldwide. Intracellular neurofibrillary tangles and extracellular senile plaques, primarily in the hippocampus and cerebral cortex, are two characteristic features of the disease. The main component of the extracellular plaques is β-amyloid (Aβ), a proteolytic product of amyloid precursor protein (APP). When cleaved from APP, Aβ spontaneously self-assembles into soluble oligomers that progress into insoluble fibrillar aggregates. Although the precise mechanism of AD pathogenesis is unknown, several studies have suggested that the aggregation of Aβ plays a key causal role, and that the soluble oligomers are the most toxic Aβ species (Roychaudhuri et al., 2009, Haass and Selkoe, 2007; Lesnê et al., 2006).

Numerous small molecules that can alter Aβ production and/or aggregation have been explored as therapeutic agents against AD, although to date none have been clinically effective (Karran et al., 2011). As an alternative approach, the use of peptides and peptidomimetics that bind to Aβ and alter Aβ aggregation was introduced, since peptides have potential advantages over small molecules in terms of better target affinity and specificity (Craik et al., 2013). In general, peptides that bind to Aβ have been either designed based on self-complementary domains, or found by screening random-peptide libraries (Takahashi and Mihara, 2008, Tjernberg et al., 1996; Taylor et al., 2010; Soto et al., 1998). Alternatively, one could design a peptide by mimicking the binding epitope of a complementary binding protein. Molecular recognition involving proteins is often mediated by relatively large interfaces with secondary structural motifs such as β-hairpins and α-helices, and thus has the potential for higher specificity than small-molecule binders. Peptides mimicking the three-dimensional structure of protein binding sites have been recognized as a promising alternative, as inhibitors of protein-protein interactions, to large biologics such as antibodies (Robinson, 2008; Eichler, 2008). This approach is in particular useful when one has precise structural information about the protein-protein interaction site.

Transthyretin (TTR) is a stably-folded homotetrameric transport protein that circulates in blood and cerebrospinal fluid. TTR has been shown to be neuroprotective in AD mouse models (Stein and Johnson, 2002; Buxbaum et al., 2008; Stein et al., 2004). The inventors and others have shown that TTR binds to Aβ and inhibit its toxicity in vitro (Giunta et al., 2005; Li et al., 2011). Inhibition of toxicity is mediated at as low as 1:100 TTR:Aβ molar ratio, implying that TTR is selective for toxic Aβ oligomers (Yang et al., 2013). A peptide mimicking the epitope of Aβ-TTR interaction might therefore have a great therapeutic potential.

Previously, the inventors identified two putative binding sites on TTR: strand G in the inner hydrophobic pocket and solvent exposed EF helix (Du et al., 2012). They further analyzed the binding domain on strand G to determine the minimum requirement for binding, and synthesized a 16-mer linear peptide, G16, with the sequence of this binding domain. G16 bound Aβ and was protective against Aβ toxicity in vitro, but required a much higher concentration than TTR to afford the same level of protection. In addition, G16 differed substantially from TTR in its effect on Aβ aggregation (Cho et al., 2014).

SUMMARY OF THE INVENTION

Thus, in accordance with this disclosure, there is provided a cyclized peptide comprising the sequence SKVVTPPRYTIAALLSPYSYSQ (SEQ ID NO: 1), or a variant thereof as defined herein. The cyclized peptide may have the P residue at position 6 of SEQ ID NO: 1 as a D-amino acid. Also provided is a composition of matter comprising (i) a cyclized peptide comprising the sequence SKVVTPPRYTIAALLSPYSYSQ (SEQ ID NO: 1), or a variant thereof as defined herein, wherein said terminal S or T and Q residues are covalently bonded to each other, and (ii) a pharmaceutical buffer, carrier, diluent or excipient. The cyclized peptide may have the P residue at position 6 of SEQ ID NO: 1 as a D-amino acid. The composition may be formulated for delivery via injection or inhalation.

In another embodiment, there is provided a method of producing a cyclized peptide comprising the sequence SKVVTPPRYTIAALLSPYSYSQ (SEQ ID NO: 1), or a variant thereof as defined herein, wherein said terminal S or T and Q residues are covalently bonded to each other, said method comprising the steps of:

(a) coupling Fmoc-D-Glu-ODmab to a resin through the unprotected side chain;
(b) assembling the peptide backbone using standard solid-phase synthesis;
(c) deprotecting the Dmab protecting group;
(d) performing on-resin cyclization with an equimolar amount of benzotriazol-1-yl-N-oxy-tris(pyrrolidino)-phosphonium hexafluorophosphate; and
(e) cleaving peptide from resin using a cleavage cocktail.

The resin may be a Fmoc-PAL-PEG-PS resin. Deprotecting may comprise treatment with 2% hydrazine monohydrate in dimethylformamide followed by treatment with 10% diisopropylethylamine in dimethylformamide. Step (d) may comprise treatment for at least 12 hours, and more particularly about 18 hours, including a range of about 12-18 hours. Step (e) may comprise use of a cleavage cocktail comprising of 81.5% trifluoroacetic acid, 5% thioanisole, 5% phenol, 5% water and 2.5% ethanedithiol, optionally for 4 hours.

In still another embodiment, there is provided a method of protecting neurons from Aβ toxicity in a subject comprising administering to said subject a cyclized peptide comprising the sequence SKVVTPPRYTIAALLSPYSYSQ (SEQ ID NO: 1), or a variant thereof as defined herein. The cyclized peptide may have the P residue at position 6 of SEQ ID NO: 1 as a D-amino acid. The subject may be a human or a non-human mammal. The human subject may be diagnosed as having Alzheimer's Disease, suspected as having Alzheimer's Disease, or be genetically at risk of developing Alzheimer's Disease. The animal subject may comprise an animal model for Alzheimer's Disease.

The cyclized peptide may be administered via injection, via nasal inhalation or orally. The cyclized peptide may be administered multiple times, such as administered daily. The method may further comprise administering to said subject a second agent that (i) abrogates Aβ toxicity, such as a γ- or β-secretase inhibitor, or an inhibitor of $A\beta_{42}$ levels, or (ii) a cognition improving agent.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the disclosure, and vice versa. Furthermore, compositions and kits of the disclosure can be used to achieve methods of the disclosure.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present disclosure. The disclosure may be better understood by reference to one or more of these drawings in combination with the detailed description of the disclosure that follows.

FIGS. 1A-C. Cyclic peptide design strategy. (FIG. 1A) Ribbon structure of transthyretin (PDB entry 1DVQ) monomer, showing strands G and H in blue. Sidechains from residues 102 to 125 are shown explicitly (SEQ ID NO: 15). Leu110, a critical residue for interaction is shown in red. Sequence of strands G and H is shown, with the boxed region corresponding to the sequence of G16 (SEQ ID NO: 10). (FIG. 1B) Design of cyclic peptides CG2 (SEQ ID NO: 12) and CG3 (SEQ ID NO: 13), mimicking the hairpin structure of strand G/loop/strand H using a dipeptide $^D$Pro-$^L$Pro template (green box). Residues in red boxes are changed from the native sequence for the cyclization process. (FIG. 1C) Idealized structure of CG3. Amino acids in green color are on one face and those in blue color are on the opposite face of the two-stranded β-sheet. The 'green' face is hypothesized to be important for Aβ binding.

FIGS. 2A-B. Purification and characterization of β-hairpin peptides LG3 and CG3. (FIG. 2A) RP-HPLC (FIG. 2B) Circular dichroic spectra.

FIG. 3. Gel electrophoresis analysis of photoinduced cross-linked (XL) and uncrosslinked (Non-XL) peptides. Peptide concentration was 36 μM, and peptides were visualized by silver staining Non-cross-linked CG3 and LG3 were boiled and separated on the right two lanes for comparison.

FIGS. 4A-B. Evidence of interaction between Aβ and peptides investigated by photo-induced cross-linking (PI-CUP). (FIG. 4A) Aβ was incubated without (−) or with peptides G16, CG3, LG3, CG2, LG2 and GF where Aβ concentration is in 10-fold excess. Samples were crosslinked prior to application to gels. Aβ was detected via Western blotting with 4G8. (FIG. 4B) Aβ at different aggregation state (freshly prepared or pre-aggregated) was incubated without (−) or with peptides G16 and CG3 prior to cross-linking and electrophoresis. Aβ was detected via Western blotting FIG. 5. Evidence of interaction between Aβ and peptides investigated by proteolytic fragmentation assay. Aβ was incubated with or without G16, CG3, LG3, CG2 and GF for 24 hr where peptide is in 3-fold excess. The relative rate of proteolytic fragmentation of Aβ was measured by addition of Proteinase K followed by dotting onto nitrocellulose membrane at different time points. Unfragmented species were detected by 6E10 and 4G8 antibodies.

FIGS. 9A-F. TEM images, taken after 48 h incubation at 37° C. (FIGS. 9A and 9B) 28 μM Aβ, (FIG. 9C) 28 μM Aβ+2.8 µM G16, and (FIGS. 9D-F) 28 µM Aβ+2.8 µM CG3. Scale bar for FIGS. 8A and 8D is 500 nm and for FIGS. 8B, 8C, 8E and 8F is 200 nm.

FIGS. 10A-D. Effect of peptides on Aβ induced toxicity measured using the MTS assay with primary neuronal cultures. Aβ concentration was 10 µM. Dose-dependent protection afforded by (FIG. 10A) mTTR (FIG. 10B) G16, (FIG. 10C) CG3. (FIG. 10D) Comparison of efficacy of several peptides, all at 10 µM. *statistically different from vehicle (p<0.05). #statistically different from Aβ (p<0.05)

DETAILED DESCRIPTION OF ILLUSTRATIVE EMBODIMENTS

Figure 5:
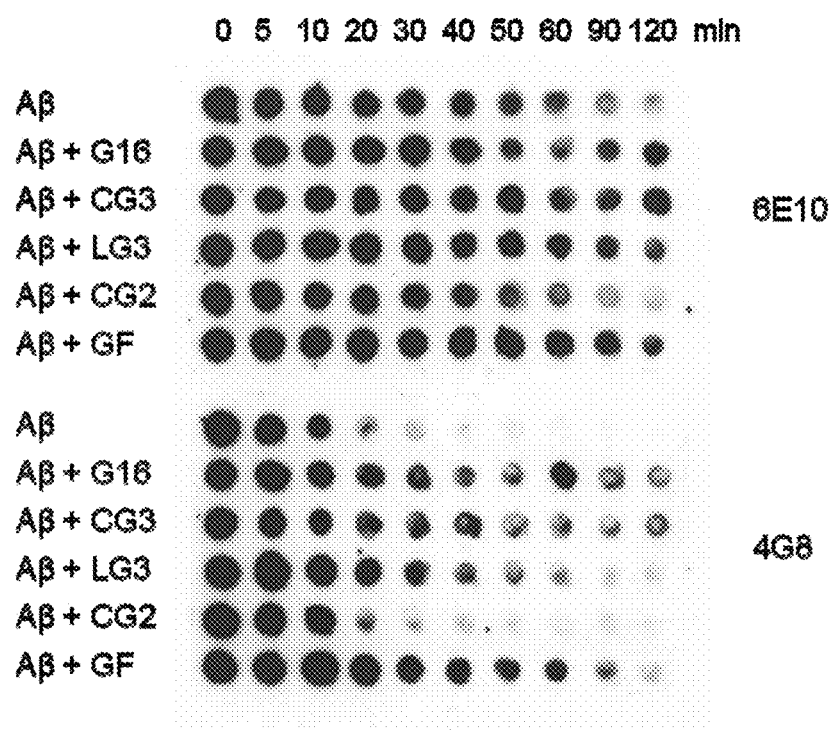

Self-association of β-amyloid (Aβ) into soluble oligomers and fibrillar aggregates is associated with Alzheimer's disease (AD) pathology, motivating the search for compounds that selectively bind to and inhibit Aβ oligomerization and/or neurotoxicity. Numerous small molecules that can alter Aβ production and/or aggregation have been extensively explored as therapeutic agents against AD, although to date none have been clinically effective. An alternative approach is to exploit the use of peptides and peptidomimetics that bind to Aβ, since peptides have potential advantages over small molecules in terms of better target affinity and specificity. Two strategies have been employed by several researchers in the search for peptides that bind to Aβ: (i) using self-complementation; and (ii) screening random peptide-based libraries.

The inventors employed a third, different strategy by designing Aβ-binding peptides based on knowledge of complementary binding proteins. Transthyretin (TTR), a plasma transport protein that is also abundant in cerebrospinal fluid, has been shown to bind to Aβ and inhibit its toxicity, both in vitro and in vivo. TTR was first identified based on its neuroprotective activity, and only later was it shown that neuroprotection was mediated via direct binding to Aβ oligomers. Thus, this strategy is a departure from prior peptide design efforts, where binding (rather than evidence of neuroprotection) was the initial basis for design.

Previously, the inventors identified strand G of TTR as a specific Aβ binding domain, and they synthesized and tested several peptides derived from this TTR sequence. G16, a 16-mer peptide containing a sequence identical to that of strand G of human TTR, was shown to be protective against Aβ toxicity. However, although both TTR and G16 bind to Aβ and inhibit toxicity, G16 was about 25-fold less effective than full-length TTR at protecting cells from Aβ toxicity.

The inventors hypothesized that the gap in efficacy between native TTR and G16 could be attributed to the fact that G16 was a sequence but not structural mimic of the Aβ binding domain on TTR. G16 spans two β-strands on TTR (strand G and H) plus a short connecting loop. However, G16 lacks the β-strand/loop/β-strand structure of the binding domain in TTR. The register of a β-hairpin structure determines which pairs of cross-strand amino acids participate in hydrogen bonding and this in turn defines which side chains are displayed on the same face of the hairpin. Various templates have been used to mimic the alignment of anti-parallel strands connected by a loop; the most straightforward approach is to transplant anti-parallel β-strands onto a semirigid hairpin-stabilizing template.

In an effort to bridge the gap in efficacy between native TTR and G16, the inventors took the concept one step further by mimicking not only the sequence of the binding epitope, but also its structure. To mimic the alignment of each residue in the binding epitope, they designed a cyclic peptide where a hairpin turn is enforced via a dipeptide D-Pro-L-Pro. Two cyclic peptides with 18 and 22 amino acids were synthesized using an orthogonally protected glutamic acid derivative and solid-phase synthesis. Synthesis and cyclization were confirmed by mass spectrometry and circular dichroism.

The inventors then examined the ability to bind to Aβ by photo-induced cross-linking and proteolytic fragmentation. The first peptide that was successfully synthesized and cyclized, CG2, contained 18 amino acids. However, they found that CG2 did not bind Aβ. They then modified the design and synthesized a cyclic 22-mer, CG3, and found that cycG3 strongly interacted with Aβ. The inventors next evaluated the effect of cyclic peptides on Aβ aggregation kinetics by dynamic light scattering. The cyclic peptide increased both the average hydrodynamic size and the rate of growth of Aβ aggregates, and the effect was much stronger than that of G16. Finally, they observed that CG3 was able to protect neurons against Aβ toxicity at relatively low concentration. Thus, CG3 constitutes a lead example of therapeutic biological compounds with activity against Aβ toxicity.

These and other aspects of the disclosure are described in detail below.

I. TRANSTHYRETIN

Transthyretin (TTR) is a serum and cerebrospinal fluid carrier of the thyroid hormone thyroxine (T4) and retinol-binding protein bound to retinol. This is how transthyretin gained its name, transports thyroxine and retinol. The liver secretes transthyretin into the blood, and the choroid plexus secretes TTR into the cerebrospinal fluid. TTR was originally called prealbumin (or thyroxine-binding prealbumin) because it ran faster than albumin on electrophoresis gels.

In cerebrospinal fluid TTR is the primary carrier of T4. TTR also acts as a carrier of retinol (vitamin A) through its association with retinol-binding protein (RBP) in the blood and the CSF. Less than 1% of TTR's T4 binding sites are occupied in blood, which is taken advantage of below to prevent TTRs dissociation, misfolding and aggregation which leads to the degeneration of post-mitotic tissue.

Numerous other small molecules are known to bind in the thyroxine binding sites, including many natural products (such as resveratrol), drugs (Tafamidis, or Vyndaqel, diflunisal, flufenamic acid), and toxins (PCB).

TTR is a 55 kDa homotetramer with a dimer of dimers quaternary structure that is synthesized in the liver, choroid plexus and retinal pigment epithelium for secretion into the bloodstream, cerebrospinal fluid and the eye, respectively. Each monomer is a 127-residue polypeptide rich in beta sheet structure. Association of two monomers via their edge beta-strands forms an extended beta sandwich. Further association of two of these dimers in a face-to-face fashion produces the homotetrameric structure and creates the two thyroxine binding sites per tetramer. This dimer-dimer interface, comprising the two T4 binding sites, is a weaker interface than the monomer-monomer interface, and is the one that comes apart first in the process of tetramer dissociation. Transthyretin has been shown to interact with Perlecan.

TTR misfolding and aggregation is known to be associated with the amyloid diseases senile systemic amyloidosis (SSA), familial amyloid polyneuropathy (FAP), and familial amyloid cardiomyopathy (FAC). TTR tetramer dissociation is known to be rate-limiting for amyloid fibril formation. However, the monomer also must partially denature in order for TTR to be mis-assembly competent, leading to a variety of aggregate structures, including amyloid fibrils.

While wild-type TTR can dissociate, misfold, and aggregate, leading to SSA, point mutations within TTR are known to destabilize the tetramer composed of mutant and wild-type TTR subunits, facilitating more facile dissociation and/or misfolding and amyloidogenesis. A replacement of valine by methionine at position 30 (TTR V30M) is the mutation most commonly associated with FAP. A position 122 replacement of valine by isoleucine (TTR V122I) is carried by 3.9% of the African-American population, and is the most common cause of FAC. SSA is estimated to affect over 25% of the population over age 80. Severity of disease varies greatly by mutation, with some mutations causing disease in the first or second decade of life, and others being more benign. Deposition of TTR amyloid is generally observed extracellularly, although TTR deposits are also clearly observed within the cardiomyocytes of the heart.

Treatment of familial TTR amyloid disease has historically relied on liver transplantation as a crude form of gene therapy. Because TTR is primarily produced in the liver, replacement of a liver containing a mutant TTR gene with a normal gene is able to reduce the mutant TTR levels in the body to <5% of pretransplant levels. Certain mutations, however, cause CNS amyloidosis, and due to the their production by the choroid plexus, the CNS TTR amyloid diseases do not respond to gene therapy mediated by liver transplantation.

In 2011, the European Medicines Agency approved Tafamidis or Vyndaqel for the amelioration of FAP. Vyndaqel kinetically stabilizes the TTR tetramer, preventing tetramer dissociation required for TTR amyloidogenesis and subsequent degradation of the autonomic nervous system and/or the peripheral nervous system and/or the heart.

TTR is also thought to have beneficial side effects, by binding to the infamous beta-amyloid protein, thereby preventing beta-amyloid's natural tendency to accumulate into the plaques associated with Alzheimer's Disease. Preventing plaque formation is thought to enable a cell to rid itself of this otherwise toxic protein form and, thus, help prevent and maybe even treat the disease.

There is now strong genetic and pharmacologic data indicating that the process of amyloid fibril formation leads to the degeneration of post-mitotic tissue causing FAP and likely FAC and SSA. Evidence points to the oligomers generated in the process of amyloidogenicity leading to the observed proteotoxicity.

Transthyretin level in cerebrospinal fluid has also been found to be lower in patients with some neurobiological disorders such as schizophrenia. The reduced level of transthyretin in the CSF may indicate a lower thyroxine transport in brains of patients with schizophrenia. Because transthyretin is made in part by the choroid plexus, it can be used as an immunohistochemical marker for choroid plexus papillomas.

II. PEPTIDE INHIBITOR

A. Structure

The present disclosure describes the design, production and use of various Aβ binding peptides derived from TTR that inhibit Aβ-associated neurotoxicity. The structural features of these peptides are as follows. First, the peptides will generally have no more than 30 consecutive residues, and more particularly be 22 residues in length. Thus, a claim direct to "a peptide having no more than 22/30 consecutive residues," even when including the term "comprising," cannot be understood to comprise a greater number of residues. Second, the peptides will contain the motifs responsible for interaction with Aβ. In general, the peptides will have, at a minimum, SKVVTPPRYTIAALLSPYSYSQ (SEQ ID NO: 1) and substitutions thereof.

Thus, the peptides will be 22-30 residues in length, again, comprising no more than 30 consecutive residues of a TTR. The overall length may be 22, 23, 24, 25, 26, 27, 28, 29, or 30 residues. Ranges of peptide length of 22-30 residues, 23-30 residues, 24-30 residues, 25-30 residues, 26-30 residues, 27-30 residues, 28-30 residues, or 29-30, residues are contemplated.

The present peptides may utilize L-configuration amino acids, D-configuration amino acids, or a mixture thereof. While L-amino acids represent the vast majority of amino acids found in proteins, D-amino acids are found in some proteins produced by exotic sea-dwelling organisms, such as cone snails. They are also abundant components of the peptidoglycan cell walls of bacteria. D-serine may act as a neurotransmitter in the brain. The L and D convention for amino acid configuration refers not to the optical activity of the amino acid itself, but rather to the optical activity of the isomer of glyceraldehyde from which that amino acid can theoretically be synthesized (D-glyceraldehyde is dextrorotary; L-glyceraldehyde is levorotary). In particular, the inventors have substituted one of the prolines (e.g., position 6 of SEQ ID NO: 1) with a D-amino acid.

The peptides of the present disclosure are cyclized. Any method of cyclization may be employed. In particular, the inventors have linked the terminal residues of the linear sequence SKVVTPPRYTIAALLSPYSYSQ (SEQ ID NO: 1). The process involves coupling Fmoc-D-Glu-ODmab to Fmoc-PAL-PEG-PS resin through the unprotected side chain followed by the assembly of the peptide backbone using standard Fmoc solid-phase method. Deprotecting of the Dmab protecting group is achieved by treating with 2% hydrazine monohydrate in dimethylformamide followed by the treatment with 10% diisopropylethylamine in dimethylformamide. Then, on-resin cyclization is achieved by treating with equimolar amount of PyBOP [benzotriazol-1-yl-N-oxy-tris(pyrrolidino)-phosphonium hexafluorophosphate] for 18 hr. Finally, cleavage of the peptide from the resin is achieved by treatment with cleavage cocktail comprised of 81.5% trifluoroacetic acid, 5% thioanisole, 5% phenol, 5% water and 2.5% ethanedithiol for 4 hr. This method is exemplary in nature and not to be construed as limiting.

B. Variants

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Thus, in some embodiments, variants of SEQ ID NO: 1 are envisioned. These variants are generally defined the following sequence:

(SEQ ID NO: 2)
SKVVTPXRYXIAALLXPYXXXQ where X is a conservative substitution of the natural residues at that location. The number of such conservative mutations may be 1, 2, 3, 4, 5 or 6.

Conservative substitutions are well known in the art and include, for example, the changes of: alanine to serine;

arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine or alanine; threonine to serine or alanine; tryptophan to tyrosine; tyrosine to tryptophan or phenylalanine; proline to glycine; and valine to isoleucine or leucine. In particular, the present disclosure contemplates substitute of serine and threonine with alanine, proline to glycine, and tyrosine with tryptophan:

SKVVTPPRYAIAALLSPYSYSQ (SEQ ID NO: 3)

SKVVTPPRYTIAALLAPYSYSQ (SEQ ID NO: 4)

SKVVTPPRYTIAALLSPYAYSQ (SEQ ID NO: 5)

SKVVTPPRYTIAALLSPYSYAQ (SEQ ID NO: 6)

SKVVTPPRYTIAALLSPYSWSQ (SEQ ID NO: 7)

SKVVTPGRYTIAALLSPYSYSQ (SEQ ID NO: 8)

It is also understood that some amino acid substitutions may be desirable to confer improvements in the properties or performance of the cyclic peptide. Examples of these substitutions include changes in that enforce a tighter β sheet structure or that reduce the hydrophobicity of the peptide. Specific examples include:

TKVVTPPRYTIAALLSPYSYSQ (SEQ ID NO: 16)

Serine to threonine is generally considered a conservative substitution, but the branched nature of the threonine side chain motivated us, in our first synthesis, to use a serine in the first position rather than threonine, to make the cyclization reaction more efficient. Now we have gone back and successfully synthesized SEQ ID NO: 9 (cyclized). This change is anticipated to increase the β sheet tendency in this position and thereby improve performance.

SKVVTPPRYTIAKLLSPYSYSQ (SEQ ID NO: 17)

This nonconservative substitution of an alanine for a lysine in this particular position is designed to enhance lysine-tyrosine interactions across the two β strands and thereby stabilize the desired β sheet conformation. This change also increases the hydrophilicity of the peptide modestly, which is anticipated to decrease the extent of self-aggregation and thereby improve performance.

SKVVTPPRYTIAALSSPYSYSQ (SEQ ID NO: 18)

This nonconservative substitution of a leucine to a serine in this particular position is designed to enhance the hydrophilicity of the peptide without unduly altering the desired conformation. This is anticipated to decrease the extent of self-aggregation and thereby improve performance.

Also, any combination of the 2 or all 3 of the above substitutions is also possible, e.g.

TKVVTPPRYTIAKLLSPYSYSQ (SEQ ID NO: 19)

TKVVTPPRYTIAALSSPYSYSQ (SEQ ID NO: 20)

TKVVTPPRYTIAKLSSPYSYSQ (SEQ ID NO: 21)

SKVVTPPRYTIAKLSSPYSYSQ (SEQ ID NO: 22)

In making substitutional variants, the hydropathic index of amino acids may be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte & Doolittle, 1982), these are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

C. Synthesis

It will be advantageous to produce peptide backbones prior to cyclization using the solid-phase synthetic techniques (Merrifield, 1963). Other peptide synthesis techniques are well known to those of skill in the art (Bodanszky et al., 1976; Peptide Synthesis, 1985; Solid Phase Peptide Synthelia, 1984). Appropriate protective groups for use in such syntheses will be found in the above texts, as well as in Protective Groups in Organic Chemistry, 1973. These synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

Using solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptides of the disclosure are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

Aside from the 20 standard amino acids can be used, there are a vast number of "non-standard" amino acids. Two of these can be specified by the genetic code, but are rather rare in proteins. Selenocysteine is incorporated into some proteins at a UGA codon, which is normally a stop codon. Pyrrolysine is used by some methanogenic archaea in enzymes that they use to produce methane. It is coded for with the codon UAG. Examples of non-standard amino acids that are not found in proteins include lanthionine, 2-aminoisobutyric acid, dehydroalanine and the neurotransmitter gamma-aminobutyric acid. Non-standard amino acids often occur as intermediates in the metabolic pathways for standard amino acids—for example ornithine and citrulline occur in the urea cycle, part of amino acid catabolism. Non-standard amino acids are usually formed through modifications to standard amino acids. For example, homocysteine is formed through the transsulfuration pathway or by the demethylation of methionine via the intermediate metabolite S-adenosyl methionine, while hydroxyproline is made by a posttranslational modification of proline.

III. METHODS OF TREATMENT

The present disclosure provides methods of treating various disease states by administering cyclized peptides of the present disclosure to a subject. For the purposes of the present application, treatment comprises reducing one or more of the symptoms associated with the disease states discussed below. Any level of improvement will be considered treatment, and there is no requirement for a particular level of improvement or a "cure." It is also sufficient in treatment that symptoms be stabilized, i.e., that the disease condition will not worsen.

A. Aβ Formation and Neurodegenerative Disease

Amyloid-beta (Aβ or Abeta) denotes peptides of 36-43 amino acids that are crucially involved in Alzheimer's disease as the main component of the amyloid plaques found in the brains of Alzheimer patients. The peptides result from the amyloid precursor protein (APP), which is being cut by certain enzymes to yield Aβ. Aβ molecules can aggregate to form flexible soluble oligomers which may exist in several forms. It is now believed that certain misfolded oligomers (known as "seeds") can induce other Aβ molecules to also take the misfolded oligomeric form, leading to a chain reaction. The seeds or the resulting amyloid plaques are toxic to nerve cells. The other protein implicated in Alzheimer's disease, tau protein, also forms such misfolded oligomers, and there is some evidence that misfolded Aβ can induce tau to misfold.

The normal function of Aβ is not well understood. Though some animal studies have shown that the absence of Aβ does not lead to any loss of physiological function, several potential activities have been discovered for Aβ, including activation of kinase enzymes, protection against oxidative stress, regulation of cholesterol transport, functioning as a transcription factor, and anti-microbial activity (potentially associated with Aβ's pro-inflammatory activity). The glymphatic system clears metabolic waste from the mammalian brain, and in particular beta amyloids. The rate of removal is significantly increased during sleep.

Aβ is the main component of amyloid plaques (extracellular deposits found in the brains of patients with Alzheimer's disease). Similar plaques appear in some variants of Lewy body dementia and in inclusion body myositis (a muscle disease), while Aβ can also form the aggregates that coat cerebral blood vessels in cerebral amyloid angiopathy. The plaques are composed of a tangle of regularly ordered fibrillar aggregates called amyloid, a protein fold shared by other proteins such as the prions associated with protein misfolding diseases. Recent research suggests that soluble oligomeric forms of the peptide may be causative agents in the development of Alzheimer's disease. It is generally believed that Aβ oligomers are the most toxic. A number of genetic, cell biology, biochemical and animal studies support the concept that Aβ plays a central role in the development of Alzheimer's disease pathology.

Brain Aβ is elevated in patients with sporadic Alzheimer's disease. Aβ is the main constituent of brain parenchymal and vascular amyloid; it contributes to cerebrovascular lesions and is neurotoxic. It is unresolved how Aβ accumulates in the central nervous system and subsequently initiates the disease of cells. Some researchers have found that the Aβ oligomers induce some of the symptoms of Alzheimer's Disease by competing with insulin for binding sites on the insulin receptor, thus impairing glucose metabolism in the brain. Significant efforts have been focused on the mechanisms responsible for Aβ production, including the proteolytic enzymes β- and γ-secretases which generate Aβ from its precursor protein, APP (amyloid precursor protein). Aβ circulates in plasma, cerebrospinal fluid (CSF) and brain interstitial fluid (ISF) mainly as soluble Aβ40. Senile plaques contain both Aβ40 and Aβ42, while vascular amyloid is predominantly the shorter Aβ40. Several sequences of Aβ were found in both lesions. Generation of Aβ in the CNS may take place in the neuronal axonal membranes after APP-mediated axonal transport of β-secretase and presenilin-1.

Increases in either total AO levels or the relative concentration of both $Aβ_{40}$ and $Aβ_{42}$ (where the former is more concentrated in cerebrovascular plaques and the latter in neuritic plaques) have been implicated in the pathogenesis of both familial and sporadic Alzheimer's disease. Due to its more hydrophobic nature, the Aβ42 is the most amyloidogenic form of the peptide. However the central sequence KLVFFAE (SEQ ID NO: 23) is known to form amyloid on its own, and probably forms the core of the fibril.

The hypothesis, that insoluble Aβ fibrils and plaques are responsible for the pathology of Alzheimer's disease, was at one time accepted by the majority of researchers but has by no means been conclusively established. An alternative hypothesis is that soluble amyloid oligomers rather than plaques are responsible for the disease. Mice that are genetically engineered to express oligomers but not plaques ($APP^{E693Q}$) develop the disease. Furthermore mice that are in addition engineered to convert oligomers into plaques ($APP^{E693Q}$ × PS1ΔE9), are no more impaired than the oligomer only mice. Intra-cellular deposits of tau protein are also seen in the disease, and may also be implicated, as has aggregation of alpha synuclein.

Aβ is formed after sequential cleavage of the amyloid precursor protein (APP), a transmembrane glycoprotein of undetermined function. APP can be cleaved by the proteolytic enzymes α-, β- and γ-secretase; Aβ protein is generated by successive action of the β and γ secretases. The γ secretase, which produces the C-terminal end of the Aβ peptide, cleaves within the transmembrane region of APP and can generate a number of isoforms of 36-43 amino acid residues in length. The most common isoforms are $Aβ_{40}$ and $Aβ_{42}$; the longer form is typically produced by cleavage that occurs in the endoplasmic reticulum, while the shorter form is produced by cleavage in the trans-Golgi network. The $Aβ_{40}$ form is the more common of the two, but $Aβ_{42}$ is the more fibrillogenic and is thus associated with disease states. Mutations in APP associated with early-onset Alzheimer's have been noted to increase the relative production of $Aβ_{42}$, and thus one suggested avenue of Alzheimer's therapy involves modulating the activity of β and γ secretases to produce mainly $Aβ_{40}$. Aβ is destroyed by several amyloid-degrading enzymes including neprilysin.

Amyloid beta is commonly thought to be intrinsically unstructured, meaning that in solution it does not acquire a unique tertiary fold but rather populates a set of structures. As such, it cannot be crystallized and most structural knowledge on amyloid beta comes from NMR and molecular dynamics. Early NMR-derived models of a 26-aminoacid polypeptide from amyloid beta (Aβ 10-35) show a collapsed coil structure devoid of significant secondary structure content, however, the most recent (2012) NMR structure of (Aβ 1-40) has significant secondary and tertiary structure. Replica exchange molecular dynamics studies suggested that amyloid beta can indeed populate multiple discrete structural states; more recent studies identified a multiplicity of discrete conformational clusters by statistical analysis. By NMR-guided simulations, amyloid beta 1-40 and amyloid beta 1-42 also seem to feature highly different conformational states, with the C-terminus of amyloid beta 1-42 being more structured than that of the 1-40 fragment.

Structural information on the oligomeric state of amyloid beta is still sparse as of 2010. Low-temperature and low-salt conditions allowed to isolate pentameric disc-shaped oligomers devoid of beta structure. In contrast, soluble oligomers prepared in the presence of detergents seem to feature substantial beta sheet content with mixed parallel and anti-parallel character, different from fibrils; computational studies suggest an antiparallel beta-turn-beta motif instead for membrane-embedded oligomers.

The mechanism by which amyloid beta may damage and kill neurons is not established. One hypothesis involves the generation of reactive oxygen species during the process of its self-aggregation. When this occurs on the membrane of neurons it causes lipid peroxidation and the generation of a toxic aldehyde called 4-hydroxynonenal which, in turn, impairs the function of ion-motive ATPases, glucose transporters and glutamate transporters. As a result, amyloid beta promotes depolarization of the synaptic membrane, excessive calcium influx and mitochondrial impairment.

B. Combined Therapy

In another embodiment, it is envisioned to use a cyclized peptide of the present disclosure in combination with other therapeutic modalities. Thus, in addition to the therapies described above, one may also provide to the cell, tissue or patient more "standard" pharmaceutical therapies. Combinations may be achieved by contacting cells, tissues or subjects with a single composition or pharmacological formulation that includes both agents, or by contacting the cell with two distinct compositions or formulations, at the same time, wherein one composition includes the expression construct and the other includes the agent. Alternatively, the therapy using a cyclized peptide of the present disclosure may precede or follow administration of the other agent(s) by intervals ranging from minutes to weeks. In embodiments where the other agent and cyclized peptide are applied separately to the cell, tissue or subject one would generally ensure that a significant period of time did not expire between the time of each delivery, such that the agent and cyclized peptide would still be able to exert an advantageously combined effect on the cell, tissue or subject. In such instances, it is contemplated that one would typically contact the cell, tissue or subject with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either a cyclized peptide of the present disclosure, or the other agent will be desired. In this regard, various combinations may be employed. By way of illustration, where the cyclized peptide of the present disclosure is "A" and the other agent is "B," the following permutations based on 3 and 4 total administrations are exemplary:

| A/B/A | B/A/B | B/B/A | A/A/B | B/A/A | A/B/B |
|-------|-------|-------|-------|-------|-------|
| B/B/B/A | B/B/A/B | A/A/B/B | A/B/A/B | A/B/B/A | B/A/B/A |
| B/A/B/A | B/A/A/B | B/B/B/A | A/A/A/B | B/A/A/A | A/B/A/A |
| A/A/B/A | A/B/B/B | B/A/B/B | B/B/A/B | | |

Other combinations are likewise contemplated. Non-limiting examples of a pharmacological therapeutic agents that may be used in combination with peptides of the present disclosure include γ- and β-secretase inhibitors, $A\beta_{42}$ lowering agents, NMDA antagonists, cognition enhancers, and acetyl cholinesterase inhibitors.

C. Pharmacological Therapeutic Agents

Pharmacological therapeutic agents and methods of administration, dosages, etc., are well known to those of skill in the art (see for example, the "Physicians Desk Reference," Klaassen's "The Pharmacological Basis of Therapeutics," "Remington's Pharmaceutical Sciences," and "The Merck Index, Eleventh Edition," incorporated herein by reference in relevant parts), and may be combined with the disclosure in light of the disclosures herein. Some variation in dosage will necessarily occur depending on the condition of the subject being treated. The person responsible for administration will, in any event, determine the appropriate dose for the individual subject, and such individual determinations are within the skill of those of ordinary skill in the art. Moreover, for human administration, preparations should meet sterility, pyrogenicity, general safety and purity standards as required by FDA Office of Biologics standards.

Where clinical applications are contemplated, pharmaceutical compositions will be prepared in a form appropriate for the intended application. Generally, this will entail preparing compositions that are essentially free of pyrogens, as well as other impurities that could be harmful to humans or animals. One will generally desire to employ appropriate salts and buffers to render peptides stable and allow for uptake by target cells or tissues. Buffers also will be employed when recombinant cells are introduced into a patient. Aqueous compositions of the present disclosure comprise an effective amount of the peptides, dissolved or dispersed in a pharmaceutically acceptable carrier or aqueous medium. The phrases "pharmaceutically acceptable" or "pharmacologically acceptable" refers to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present disclosure, its use in therapeutic compositions is contemplated. Supplementary active ingredients also can be incorporated into the compositions, provided they do not inactivate the vectors or cells of the compositions.

The active compositions of the present disclosure may include classic pharmaceutical preparations. Administration of these compositions according to the present disclosure may be via any common route so long as the target tissue is available via that route. This includes oral, nasal, or buccal. Alternatively, administration may be by intradermal, subcutaneous, intramuscular, intraperitoneal or intravenous injection, or by direct injection into the brain. Such compositions would normally be administered as pharmaceutically acceptable compositions, as described supra.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

For oral administration the peptides of the present disclosure generally may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including gels, pastes, powders and slurries. The active ingredient may be added in a therapeutically effective amount to a paste dentifrice that may include water, binders, abrasives, flavoring agents, foaming agents, and humectants.

The compositions of the present disclosure generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure.

IV. KITS

Any of the compositions described herein may be comprised in a kit. In a non-limiting example, a cyclized peptide is included in a kit. The kit may further include a sterile buffer to facilitate dilution. The kit may also include one or more devices for delivery, such as a syringe, catheter, inhaler or aerosol delivery device.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. The kits of the present disclosure also will typically include a means for containing the nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. However, the active agent may be provided as dried powder(s). When reagents and/or components are provided as a dry powder, the powder can be reconstituted by the addition of a suitable solvent. It is envisioned that the solvent may also be provided in another container means. Such kits may also include components that preserve or maintain the active agent that protect against its degradation.

The kits of the present disclosure will also typically include a means for containing the vials in close confinement for commercial sale, such as, e.g., injection and/or blow-molded plastic containers into which the desired vials are retained. A kit will also include instructions for employing the kit components as well the use of any other reagent not included in the kit. Instructions may include variations that can be implemented.

It is contemplated that such reagents are embodiments of kits of the disclosure. Such kits, however, are not limited to the particular items identified above and may include any reagent used for the manipulation or characterization of miRNA.

V. SCREENING METHOD

The present disclosure further comprises methods for identifying peptide inhibitors of Aβ based on TTR sequence and structure disclosed here that are useful in the prevention or treatment of the diseases discussed above. To identify an inhibitor, one generally will determine the toxicity of Aβ in the presence and absence of the candidate peptide. For example, a method generally comprises:

(a) providing a candidate peptide;
(b) admixing the candidate peptide with Aβ;
(c) measuring Aβ toxicity; and
(d) comparing the toxicity in step (c) with the toxicity in the absence of the candidate peptide,
wherein a reduction in the measured toxicity in the presence of the candidate peptide indicates that the candidate peptide is, indeed, an inhibitor of Aβ toxicity.

Assays also may be conducted in isolated cells, organs, or in living organisms.

It will, of course, be understood that all the screening methods of the present disclosure are useful in themselves notwithstanding the fact that effective candidates may not be found. The disclosure provides methods for screening for such candidates, not solely methods of finding them.

VI. EXAMPLES

The following examples are included to further illustrate various aspects of the disclosure. It should be appreciated by those of skill in the art that the techniques disclosed in the examples which follow represent techniques and/or compositions discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Materials and Methods

Peptide Synthesis and Purification.

Linear peptides (G16, GF) were synthesized using standard Fmoc solid-phase method on the Symphony peptide synthesizer (Protein Technologies, In., Tuscon, Ariz.). The resin used was Fmoc-PAL-PEG-PS from Applied Biosystems (Foster City, Calif.). Extended cycles and double couplings were used to improve yield and peptides were modified with N-terminal acetylation and C-terminal amidation. Peptides were cleaved and purified as previously described (Cho et al., 2014).

Hairpin-templated peptides (LG2, CG2, LG3, CG3) were synthesized using an orthogonally protected glutamic acid derivative and standard Fmoc solid-phase method. Fmoc-D-Glu-ODmab (Novabiochem, La Jolla, Calif.) was coupled to Fmoc-PAL-PEG-PS resin through the unprotected side chain. Assembly of the peptide backbone was done using standard Fmoc solid-phase method and the final Fmoc group was removed. The resin bound peptides were then treated with 2% hydrazine monohydrate in dimethylformamid (DMF) to remove Dmab protecting group and reacted with 10% diisopropylethylamine (DIPEA) in DMF. For peptide cyclization, an equimolar amount of PyBOP was added to the resin bound peptides, and the mixture was incubated for 18 h. Peptides were cleaved from the resin and purified by reverse-phase HPLC as previously described (Cho et al., 2014). Fractions corresponding to two major peaks (one peak containing the cyclized peptide, the other peak containing the non-cyclized peptide) were collected, lyophilized, and analyzed by matrix-assisted laser desorption/ionization time-of-flight mass spectrometry.

Purified peptides were dissolved in 0.22 µm filtered water, and the concentration of the peptides was determined by the absorbance at 205 nm with molar absorptivity calculated for each peptides based on their sequence (Anthis and Clore, 2013). Peptides were then diluted to 0.7 mM, aliquoted, snap-frozen, and stored at −80° C.

Aβ Sample Preparation.

Aβ (1-40) was purchased from Anaspec, Inc. (Fremont, Calif.) as lyophilized powder. For dynamic light scattering, ThT fluorescence assay, TEM, NTA measurement and filtration/sedimentation assay, Aβ was dissolved in 50% ACN, re-lyophilized, and reconstituted in 8M urea at 12 mg/mL. Aβ stock was then aliquoted, snap-frozen in ethanol with dry ice, and stored at −80° C. For PICUP and proteolytic fragmentation analysis, lyophilized Aβ was dissolved in prechilled hexafluoroisopropanol (HFIP, Acros Organics, Geel, Belgium), aliquoted, dried and stored at −20° C. as previously described (Cho et al., 2014). Aβ sample was prepared right before use by dissolving dried peptides in 50 mM NaOH and diluting into phosphate-buffered saline (PBSA) (10 mM $Na_2HPO_4/NaH_2PO_4$, 150 mM NaCL and 0.02% $NaN_3$ (pH 7.4)) to 30 µM as previously described (Cho et al., 2014).

Circular Dichroism.

CG3 and LG3 stock solutions in water at 0.7 mM were diluted into phosphate/NaF buffer (10 mM $K_2HPO_4/KH_2PO_4$ and 140 mM NaF (pH 7.4)) to 45 µM. Samples were filtered through 0.45 µM filter and transferred into a 1 mm cell. Circular dichroism (CD) spectra were collected on an Aviv 202SF CD spectrophotometer from Aviv Biomedical (Lakewood, N.J.) at room temperature. Blank solvent spectra were collected and subtracted.

Photoinduced Cross-Linking (PICUP) of Aβ and Peptides.

Aβ prepared with HFIP/NaOH treatment at 30 µM as described was mixed with peptides to a final concentration of 24 µM Aβ and 2.4 µM peptides. Aβ stock was used immediately (freshly prepared) or after incubation for 24 hr at 37° C. (1 day pre-aggregated). Samples of Aβ with and without peptides were incubated for 1 hr at 37° C. and cross-linked by photo-induced cross-linking method as previously described (Cho et al., 2014). Cross-linked samples were then separated on a 10-20% Tris-Tricine gradient gel (Iinvotrogen, Carlsbad, Calif.), transferred onto a 0.2 µm poly(vinylidene difluoride) (PVDF) membrane and detected by monoclonal mouse anti-Aβ antibody 4G8 (Covance, Princeton, N.J.) as previously described (Cho et al., 2014).

Peptides were also cross-linked by PICUP and analyzed for self-association. Twenty microliters of peptides at 36 µM in PBSA was incubated for 1 hr at 37° C. and cross-linked. Cross-linked samples were then heated at 95° C. for 5 min and separated on a 10-20% Tris-Tricine gradient gel. Peptides were visualized by silver staining (SilverStain Kit, Pierce, Rockford, Ill.).

Proteolytic Fragmentation Assay.

The proteolytic fragmentation assay of Aβ with peptides was performed as previously described in detail (Cho et al., 2014). Briefly, Aβ alone (20 µM) or with peptide (60 µM) was incubated for 24 hr at 37° C. Proteinase K (Promega, Madison, Wis.) was added to the samples at a final concentration of 0.5 µg/mL and samples were dotted onto a 0.45 µm nitrocellulose membrane (Pierce) after incubation for 0, 5, 10, 20, 30, 40, 50, 60, 90 and 120 min. Membranes were then reacted with monoclonal antibodies against Aβ (6E10, Covance, against Aβ (3-8) and 4G8 against Aβ (18-22)) and visualized.

Dynamic Light Scattering (DLS).

Aβ stock in 8M urea prepared as stated above was thawed and sonicated for 2 min before being diluted into PBSA. Aβ alone (140 µM) or mixed with peptides (14 µM) was filtered through 0.45 µM filter directly into a light scattering cuvette and placed into a bath of the index-matching solvent decahydronaphthalene with temperature controlled to 37° C. Light scattering data were collected using a Brookhaven BI-200SM system (Brookhaven Instruments Corp., Holtsville, N.Y.) and an Innova 90C-5 argon laser (Coherent, Santa Clara, Calif.) operating at 488 nm and 150 mW. The average scattering intensity at 90° was measured over 10 hr and data were normalized to the total mass concentration. The z-averaged hydrodynamic diameter was determined from the autocorrelation function using the method of cummulants.

Thioflavin T (ThT) Fluorescence Assay.

ThT stock solutions were prepared in PBSA and filtered through 0.22 µm filter. The concentration of ThT was measured using an extinction coefficient of 26,620 $M^{-1} cm^{-1}$ at 416 nm and the stock solution was diluted to 10 µM in PBSA prior to the measurement. Aβ alone (28 µM) and with peptides (2.8 µM) or mTTR (2.8 µM) were prepared in PBSA and incubated for 48 hr at 37° C. After 1, 5, 24 and 48 hr of incubation, 10 µL of each sample was mixed with 130 µL of 10 µM ThT and analyzed. ThT fluorescence emission was measured using a QuantaMaster spectrofluometer (PTI, Birmingham, N.J.), with excitation at 440 nm and emission spectra recorded from 460 to 500 nm. Three serial spectra were averaged for each sample and the background signal of ThT in PBSA was subtracted from the averaged data. Fluorescence intensity at a wavelength of 480 nm was compared.

Transmission Electron Microscopy (TEM).

Aβ alone (28 µM) or with peptides (G16 or CG3 at 2.8 µM) were prepared in PBSA and incubated for 48 hr at 37° C. A drop of sample was placed on a pioloform-coated grid and stained with methylamine tungstate stain. Images were taken with a Philips CM120 scanning transmission electron microscope (FEI Corp., Eindhoven, The Netherlands).

Nanoparticle Tracking (NTA).

NTA measurements were taken with a Nanosight LM10 (Nanosight, Amesbury, U.K.) equipped with a 405 nm laser as previously described (Yang et al., 2013). Aβ alone (28 µM) or with CG3 (2.8 µM) were prepared in PBSA and incubated for 5 hr at 37° C. Three 60 s video were taken for each sample.

Filtration/Sedimentation Assay.

Aβ alone (30 µM) or with CG3 (3 µM) was prepared in PBSA and incubated for 24 hr at 37° C. For filtration, 175 µL of sample was filtered through 0.45 µm filter. For sedimentation, 100 µL of sample was transferred onto a separate tube and centrifuged for 30 min at 19,500 ref. The supernatant (80%) was removed. Concentrations of untreated, filtered, and centrifuged samples were measured by BCA assay (Pierce).

Expression and Purification of mTTR.

Recombinant human transthyretin mutant F87M/L110M (mTTR) was produced and purified as previously described in detail (Du and Murphy 2010).

In Vitro Cellular Toxicity.

Aβ toxicity was assessed as described in detail previously (Yang et al., 2013; Cho et al., 2014). Briefly, the primary cortical neuronal cells were cultured from embryonic 15.5 day mice and were maintained in neurobasal media till they are matured. Aβ (1-42) (American Peptide, Sunnyvale, Calif.) at 1 mg/mL in PBS was diluted to 10 μM without or with peptides as previously described (Cho et al., 2014). At 6 days in vitro (DIV), the cells were treated with either Aβ alone or Aβ incubated with different doses of mTTR and peptides. Appropriate vehicle and controls were run along with the treatments. At 8 DIV, the neurons were incubated with MTS reagent (Promega) as per manufacturer protocol for 2-3 hrs and absorbance was measured at 490 nm.

Example 2—Results and Discussion

Design and Synthesis of Cyclic Peptides.

Strand G of TTR contains Leu110, a critical residue for binding of TTR to Aβ (FIGS. 1A-B). A linear peptide, G16, encompassing this binding domain showed moderate neuroprotective activity against Aβ toxicity (Cho et al., 2014). The inventors hypothesized that constraining the conformation of G16 would better mimic the structure of native TTR, leading to improved interaction with Aβ. Several different strategies can be employed to mimic antiparallel β-strands connected by a loop: disulfide bridge formation, turn stabilization by strong β-hairpin promoters, or cyclization. Since it was important to preserve the residues critical for interaction with Aβ, the inventors decided to make a cyclic structure by connecting the N-terminus of strand G and C-terminus of strand H using a β-hairpin stabilizing template, without modifying residues Thr106 to Ser117. There have been previous reports of successful synthesis of short peptides that mimic the hairpin-like structure of a native protein (Robinson, 2008; Milroy et al., 2014). To the best of the inventors' knowledge, there have been no prior reports of successful synthesis of a cyclic peptide containing two relatively long anti-parallel β-strands (~6-8 residues per strand). Therefore, each aspect of the synthesis of this cyclic binding-site mimic required careful consideration. A dipeptide containing $^D$Pro at position i+1 prefers to adopt β-turns with a right-handed twist (Gellman, 1998), so dipeptides such as $^D$Pro-Gly and $^D$Pro-Pro are commonly used as β-turn inducing templates (Favre et al., 1999). When transplanting a hairpin loop structure from the native protein onto a dipeptide template, it is important to insert it at a non-hydrogen bonding position to maintain the hydrogen-bonding pattern along the anti-parallel β-strands. In addition, a regular hairpin structure is only seen when the connecting strands contain in total (4n+2) residues where n is an integer (Gibbs et al., 1998). Given these considerations, the inventors decided to transplant Arg104 to Thr123 onto a turn-inducing template, as mimics of the G and H strands of TTR.

On-resin cyclization was chosen to prevent the formation of peptide oligomeric by-products. Trifunctional amino acids (glutamic or aspartic acid), where the amino acid can be anchored to the resin through the side chain, are incorporated into the sequence to allow on-resin cyclization. Although it is common practice to place the turn-inducing template in the middle of the linear sequence to enhance cyclization efficiency, the inventors wanted to preserve all the residues near the loop; therefore the glutamic acid was placed adjacent to Ser117. It was thus anticipated that the cyclization efficiency would be lower than what has been reported by others using template in the middle. After cleavage from the amide-resin the glutamic acid is converted to glutamine. The end coupling reaction occurs between the C-terminus of Gln and N-terminus of the adjacent residue, corresponding to Thr119 in the native sequence. To enhance the coupling efficiency, the branched residue Thr was changed to Ser. The residue corresponding to Ala120 was changed to Lys for two reasons: (1) to increase the solubility of the cyclic peptide without interfering with Aβ binding because it is pointing towards the opposite site of the interacting domain in the native TTR structure and (2) to increase the stability of β-hairpin via interaction with Tyr105 (Syud et al., 2001).

In the first attempt at producing a structural mimic, SKVVT$^D$PGRYTIAALLSPYSYSQ (SEQ ID NO: 9) was successfully synthesized as the linear peptide by standard Fmoc-solid phase methods. The reagent PyBOP was added for the end-coupling (cyclization) reaction. Mass spectra analysis of the reaction product showed, however, that cyclization failed, and a side product with mass 53 amu higher than the starting peptide was produced instead. Formation of this side product was traced to the presence of small amounts of pyrrolidine contaminant in PyBOP, and to the difficulty of the desired coupling (Alsina et al., 1999). Therefore, the inventors designed a second peptide where the $^D$Pro-Gly template was changed to the more rigid $^D$Pro-Pro and the length was shortened to 18 amino acids (Thr106 to Val121) to pre-organize reactive ends in closer proximity (FIG. 1B). The diproline peptide has been reported to strongly prefer a type II' β-turn backbone, and to stabilize a second opposite turn (Bean et al., 1992). Additionally, freshly crystallized PyBOP, confirmed free of pyrrolidine by mass spectrometry, was used. After 18 hr reaction with PyBOP, the inventors obtained a mixture of cyclized (CG2) and non-cyclized (LG2) peptides confirmed by mass spectrometry (not shown). With the success of CG2 synthesis, they attempted a longer peptide, and successfully synthesized a 22-residue peptide containing the $^D$Pro-Pro template, and performed on-resin cyclization (FIG. 1B). The mixture of CG3 and LG3 was separated by RP-HPLC (FIG. 2A), and the identity of the peptides in each peak was confirmed by mass spectrometry. From the HPLC peak area, the inventors estimated the yield of cyclic peptide at about 40%. Table 1 lists the sequences of TTR-derived peptides used in this study.

TABLE 1

Sequences of TTR-derived peptides

| Peptide name | Sequence | TTR residue numbers | Mol. wt (expected/ measured) | Modification from native TTR sequence |
|---|---|---|---|---|
| G16 | PRRYTIAA LLSPYSWS (SEQ ID NO: 10) | 102-117 | 1922.2/ 1922.0 | Y116W |
| GF | PRRYTIAA LLSPYSWS DYKDDDDK (SEQ ID NO: 11) | 102-117 | 2917.2/ 2916.3 | Y116W, FLAG tag added to C-terminus |
| LG2 | SKV$^D$PPTIA ALLSPYSYS Q (SEQ ID NO: 12) | 106-121 | 1921.2/ 1921.2 | T118Q, T119S, A120K Grafted onto $^D$PP template |
| CG2 | SKV$^D$PPTIA ALLSPYSYS Q (SEQ ID NO: 12) | 106-121 | 1903.2/ 1904.0 | T118Q, T119S, A120K, Grafted onto $^D$PP template, cyclized |
| LG3 | SKVVT$^D$PPR YTIAALLSP | 104-123 | 2441.8/ 2441.2 | T118Q, T119S, A120K Grafted |

TABLE 1 -continued

Sequences of TTR-derived peptides

| Peptide name | Sequence | TTR residue numbers | Mol. wt (expected/ measured) | Modification from native TTR sequence |
|---|---|---|---|---|
| | YSYSQ (SEQ ID NO: 13) | | | onto $^D$PP template |
| CG3 | SKVVT$^D$PPR YTIAALL SPYSYSQ (SEQ ID NO: 13) | 104-123 | 2423.8/ 2423.2 | T118Q, T119S, A120K, Grafted onto $^D$PP template, cyclized |

Characterization of Peptides.

A change in secondary structure due to cyclization was confirmed by circular dichroism (FIG. 2B). The decrease in the absolute molar ellipticity at 197 nm and a flattening at ~215 nm for CG3 is interpreted as an indication of formation of a β-hairpin structure and increased β-sheet content (Walters and Murphy, 2011).

Peptide self-assembly was probed by photo-induced crosslinking (PICUP) followed by gel electrophoresis. The inventors observed discrete oligomers ranging from ~24 to >45 kDa (apparent) for CG3, LG3 and CG2, similar to G16 (FIG. 3), all indicative of the tendency of these peptides to self-associate in aqueous buffers. For LG2, the oligomer distribution was shifted towards lower molecular weight. In the absence of crosslinker, G16 was observed as a faint smear at the bottom of the gel because the size of the G16 monomer is lower than the minimum of separation range (data not shown). For LG3, a clean single band was observed at the bottom of the gel. The inventors suspect that the band is the peptide monomer, although the apparent molecular weight based on the standard is larger than the actual molecular weight of the LG3 monomer (Lu et al., 2014). Interestingly, two bands were observed for CG3, suggesting that a fraction of CG3 forms a SDS-stable dimer. Finally, the inventors synthesized a linear peptide with a C-terminal FLAG tag (GF). Crosslinking of GF produced some lower-molecular-weight multimers but none of the larger multimers observed for CG3 and CG2 (FIG. 3), demonstrating that addition of a highly charged tail would reduce self-assembly.

To further probe for self-aggregation, G16, LG3, and CG3 were incubated at 80 μM at 37° C. and analyzed by light scattering. After 1 hr of incubation, LG3 did not scatter light above background, while both G16 and CG3 scattered light above background, with about 5 times higher intensity for CG3 (data not shown). Since scattering is attributed to larger particle formation, these results indicate that CG3 is the most susceptible to self-assembly, followed by G16 and then LG3.

Solution-Phase Binding of TTR-Derived Peptides to Aβ.

Two methods were used to probe for solution-phase interaction between Aβ and the cyclic peptides CG2 and CG3 and non-cyclized peptides LG2 and LG3: photo-induced cross-linking (PICUP) and proteolytic fragmentation. For comparison, G16 and GF were also tested.

Pre-aggregated Aβ (30 μM Aβ incubated for 24 hr at 37° C.) was mixed with peptides at 10:1 molar excess of Aβ, cross-linked, separated by gel electrophoresis, and detected by anti-Aβ antibody 4G8 (FIG. 4A). The inventors observed a ladder of monomer, dimer, trimer, tetramer and pentamer for Aβ alone, consistent with previous reports (Cho et al., 2014; Bitan et al., 2003). When Aβ was mixed with G16, a smear of oligomers larger than Aβ pentamers was observed, as previously reported (Cho et al., 2014). Similarly, Aβ with CG3, LG3 or GF produced a broad band of larger oligomers. In contrast, neither CG2 nor LG2 caused any shift in Aβ size distribution. The inventors interpret these data to indicate that G16, CG3, LG3 and GF all interact with Aβ, while CG2 and LG2 do not show signs of interaction with Aβ. A closer examination of the gel suggests that the interaction of Aβ with LG3 is weaker compared to CG3.

The cross-linking experiment was repeated but with freshly prepared as well as pre-aggregated Aβ (FIG. 4B). With G16 added to either fresh or pre-aggregated Aβ, a similar shift towards higher molecular weight oligomers was observed. In contrast, CG3 had much less interaction with freshly prepared Aβ than with pre-aggregated Aβ. This result suggests greater selectivity of CG3 for pre-aggregated than for freshly prepared Aβ, whereas G16 showed no such selectivity. The inventors hypothesize that the conformational constraint imposed by cyclization results in a peptide that is less adaptable and therefore more rigid in its geometric requirements for binding. The inventors previously reported that TTR preferentially interacts with soluble oligomers of Aβ rather than monomers (Yang et al., 2013); these data suggest that CG3 is a better structural mimic of TTR and therefore retains the higher selectivity for Aβ oligomers of the native folded protein.

Evidence for interaction between Aβ and peptides was also sought using a proteolytic fragmentation assay. Peptides were mixed with Aβ at 3:1 molar excess of peptides, and then protease was added. Aliquots were removed at defined time points and degradation of Aβ was assessed by probing with anti-Aβ antibody. The inventors anticipated that binding of peptides to Aβ would inhibit access of proteases and delay the degradation rate. Two monoclonal antibodies were used, which bind to either N-terminal (6E10) or central (4G8) domains of Aβ. As shown in FIG. 5, Aβ degradation was detected within 30 min by 4G8. When incubated with G16, CG3, LG3 or GF, Aβ degradation was delayed. G16 and CG3 were most effective in inhibiting degradation, followed by GF and LG3. CG2 did not have any effect on the time course of degradation. The N-terminal domain (6E10) was protected from protease for longer times overall, but the same effects of peptides were shown after 120 min. These results are consistent with the cross-linking studies (FIG. 4A), indicating that G16, CG3, LG3, and GF interact with Aβ while CG2 and LG2 do not. Why does CG2 not interact with Aβ while CG3 does? The critical residues, TIAALLSPYSYS (SEQ ID NO: 14) (Cho et al., 2014) are present in both cases. One possibility is that the β-hairpin turn in CG2 interferes sterically with binding of Aβ to T106. Or, the backbone might undergo a rearrangement so that the interacting residues appeared on the wrong face (Dias et al., 2006).

Binding of Aβ to TTR-Derived Peptides in Presence of Serum Proteins.

Figure 6:
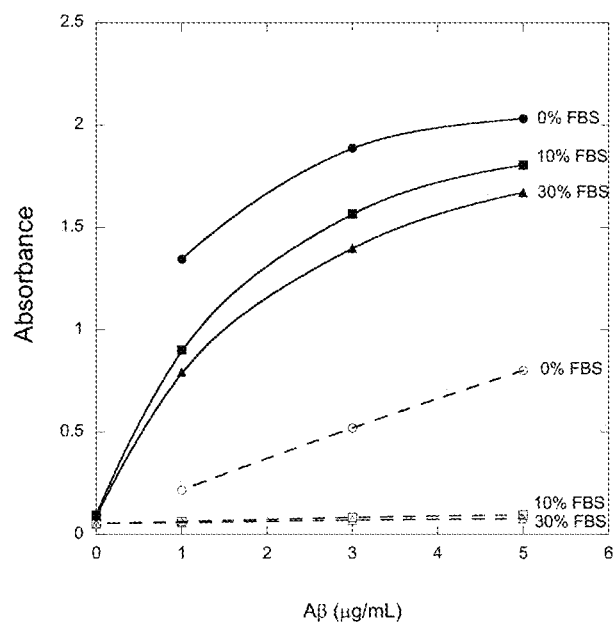
FIG. 6. Evidence of interaction between Aβ and peptide investigated by enzyme-linked immunoassay. CG3 was synthesized with an appending polyethylene glycol (PEG) linker attached to biotin. This was achieved by replacing Val at the $3^{rd}$ position with Glu and on-column addition of PEG and biotin to the Glu side chain. CG3-biotin was added to NeutrAvidin-coated ELISA plates, which immobilizes the CG3 via the biotin-NeutrAvidin interaction. After washing to remove excess CG3-biotin, Aβ at 1, 3 or 5 μg/mL was added to each well and incubated. After further washing, Aβ was detected using monoclonal anti-Aβ antibody and Superclonal-HRP. Solid symbols/solid lines are with immobilized CG3-biotin. Open symbols/dashed lines are negative control (immobilized PEG-biotin linker).

The inventors further sought to demonstrate binding of Aβ to CG3 (SEQ ID NO: 1) using an enzyme-linked immunoassay (ELISA), and in the presence of serum proteins. Briefly, CG3 was synthesized with an appended flexible PEG linker and biotin. Biotin binds tightly to streptavidin and variants (such as NeutrAvidin). NeutrAvidin coated plates were used to immobilize the biotinylated CG3, with the PEG linker providing sufficient flexibility to allow binding interactions. Aβ was prepared at 1, 3, or 5 μg/mL in PBS, or in PBS containing 10 (vol/vol) % or 30 (vol/vol) % fetal bovine serum (FBS, charcoal-treated). Protein content of FBS is typically 30-45 mg/mL, so these solutions contained roughly 1,000-fold to 10,000-fold more protein than Aβ. Aβ solutions were added to the CG3-coated wells and then incubated to allow binding. After washing, Aβ was detected by anti-Aβ antibody (6E10 or 4G8) and Superclonal-HRP. In control experiments, Aβ was added to wells with EZlink (PEG-biotin) immobilized to the NeutrAvidin instead of biotinylated CG3. As shown in FIG. 6, there was strong concentration-dependent binding of Aβ to biotinylated CG3, with approximately the same level of binding whether the solution contained 10% or 30% FBS. There was no binding of Aβ above background (buffer) levels in control wells that contained only the PEG-biotin linker. In solutions of Aβ containing no FBS, the inventors observed high levels of nonspecific binding to the PEG-biotin linker; if this nonspecific binding was subtracted from the binding to CG3, they conclude that serum proteins do not interfere with Aβ binding to CG3.

Effect of Peptides on Aβ Aggregation Kinetics.

Figure 7:
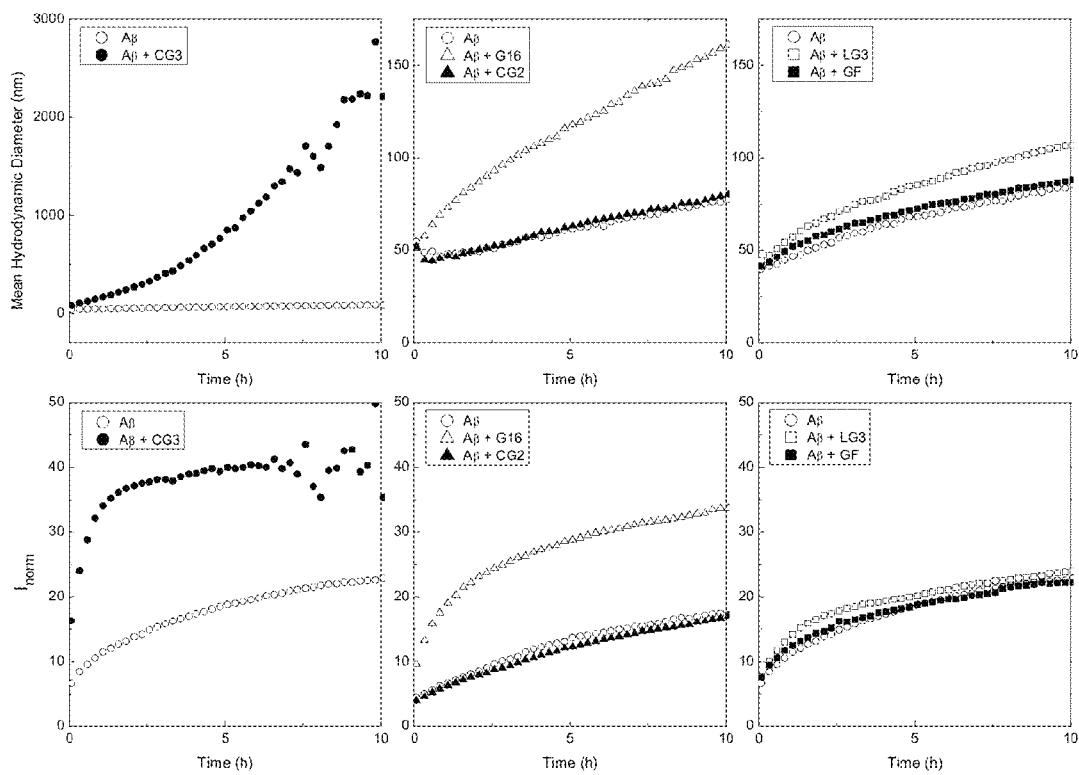
FIG. 7. Effect of peptides on Aβ aggregate growth kinetics measured by light scattering. The mean hydrodynamic diameter (top) and average scattering intensity (bottom) were measured for samples containing 140 μM Aβ without or with 14 μM CG3, LG3, CG2, G16 or GF. At the conditions of these experiments, concentrations of the peptides were too low to contribute to the scattering signal.

The inventors next evaluated whether any of the peptides influenced Aβ aggregation. For dynamic light scattering analysis, Aβ (140 μM) was prepared either alone or with added peptides, at a 10:1 molar excess of Aβ. At the low peptide concentration used for this test, there was no detectable scattering above background from the peptides in the absence of Aβ (data not shown). Aβ alone aggregated steadily over the course of 10 hours, with both the mean aggregate size and total scattered intensity increasing (FIG. 7). Both G16 and CG3 increased the size of aggregates of Aβ, but the effect of CG3 was much more pronounced. For example, after 5 hr, the mean hydrodynamic size was 1000 nm for Aβ-CG3 mixture, while that of Aβ-G16 mixture was about 120 nm. Both G16 and CG3 enhanced the intensity of scattered light similarly. To confirm the presence of large aggregates, the inventors examined the solutions using nanoparticle tracking (NTA). This technique detects scattering from individual particles as they diffuse in the optical chamber. Solutions were prepared at 28 μM Aβ and at 10:1 Aβ:peptide molar ratio. Results were consistent with DLS data: specifically, the particles detected with CG3-Aβ mixtures were very large (microns) and much larger than those of Aβ alone (data not shown).

CG2 did not show a binding interaction with Aβ in the PICUP and protease degradation assays, as mentioned above. Consistent with those results, CG2 did not affect Aβ aggregation as measured by either hydrodynamic diameter or total scattered intensity. Although LG3 and GF showed a binding interaction with Aβ in the PICUP and protease degradation assays, they had little to no effect on Aβ aggregation. The distinction between binding and effect on aggregation might be attributable to the different self-assembly characteristics of the peptides. Both G16 and CG3 readily self-assemble, as shown by PICUP (FIG. 3) and light scattering. LG3 produces oligomers similar to CG3 (FIG. 3), but did not scatter light above background at the condition (80 μM at 37° C.) where scattered light from CG3 and G16 was detectable, as previously noted. GF, presumably due to its tail of charged residues, self-assembles much less than the other peptides (FIG. 3). The inventors hypothesize that pre-organization of G16 and CG3 into larger oligomers provides a mechanism for their interaction with multiple Aβ oligomers, leading to formation of large clusters of Aβ-peptide aggregates.

As another measure of aggregation, the inventors prepared Aβ alone (30 μM) or with CG3 (10:1 Aβ excess), incubated them together for 0 or 24 hr at 37° C., then filtered through 0.45 μm filter and measured concentrations using the BCA assay. With Aβ alone, 85% of the material was filterable initially, but only 31% after 24 hours. In contrast, about 90% of the CG3-Aβ mixture was filterable at either 0 or 24 hours. Similar observations were made by sedimentation. Briefly, samples were centrifuged for 30 min and the concentration of the supernatant (top 80%) was measured. After 24 hours, only 15% of Aβ remained in the supernatant while 91% of the Aβ-CG3 mixture remains in solution. Taken together with the DLS and NTA data, this suggests that in the presence of CG3, a small fraction of Aβ is incorporated into very large aggregates, while most of it remains either unaggregated or in aggregates that are too small, diffuse, unstable, or hydrated to be removed by either centrifugation or filtration.

Figure 8:
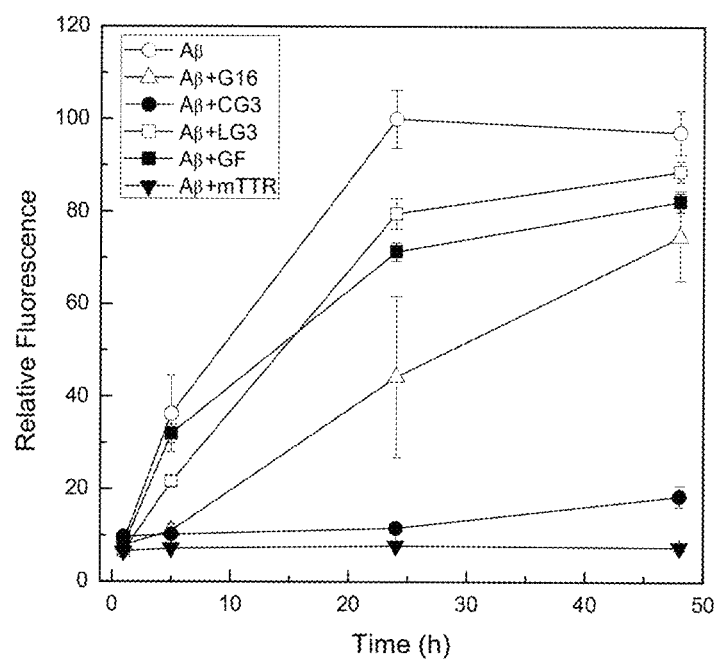
FIG. 8. Effect of peptides on Aβ aggregation measured by ThT fluorescence intensity. Samples containing 28 μM Aβ without or with 2.8 μM of the indicated peptide or protein were incubated at 37° C. for up to 48 h. After 1, 5, 24 and 48 hr of incubation, samples were diluted 14-fold into a ThT-containing solution, and fluorescence emission intensity was measured immediately. Three replicates were averaged for each sample and the data for Aβ alone, Aβ+G16 and Aβ3+CG3 represent the average of two independent experiments.

The inventors next used thioflavin T (ThT) fluorescence intensity as another measure of the effect of peptides on Aβ aggregation. ThT binds to fibrillar aggregates with a β-sheet structure but does not bind to amorphous aggregates; binding causes a sharp increase in fluorescence intensity that is proportional to the mass of fibrillar aggregates. Samples were prepared at 10:1 Aβ molar excess. After 1 hr, fluorescence intensity of all samples was low, as expected given the well-known lag time in appearance of Aβ fibrils (FIG. 8). After 5 hr, Aβ alone showed the highest ThT fluorescence intensity while that of Aβ with G16 or with CG3 remained low. A difference between G16 and CG3 appeared after 24 hr. While ThT-positive species were detected in the Aβ-G16 mixture, the fluorescence still remained low for Aβ-CG3. LG3 and GF were unable to inhibit the ThT fluorescence increase (FIG. 8), consistent with their minor effect on Aβ aggregation as measured by light scattering (FIG. 7). For comparison, ThT fluorescence of Aβ mixed with mTTR was measured. mTTR is a mutant TTR protein that is stable as a monomer and is even more effective than wild-type TTR at inhibiting Aβ aggregation (Du and Murphy, 2010). There was no increase in fluorescence observed for Aβ-mTTR even after 48 h, and it remained the sample with the lowest ThT intensity (FIG. 8). These data suggest that, of all tested peptides, CG3 is the best mimic of mTTR's aggregation inhibitory activity, but that it is not quite as effective as mTTR.

Finally, the inventors examined samples of Aβ alone or with G16 or CG3 by TEM (FIGS. 9A-F). As expected, Aβ alone aggregated into well-defined fibrils of characteristic diameter and length. With G16, there were still a large number of fibrils, many of which appeared clumped, along with numerous spherical globules, as has been previously reported (Cho et al., 2014). The CG3-Aβ sample was characterized by a strikingly lower density of aggregates (FIG. 9D). Those aggregates that were present were fibrillar but much shorter than fibrils of Aβ alone (FIGS. 9E-F). This result is in line with previously obtained TEM images of mTTR-Aβ, wherein addition of mTTR to Aβ suppressed Aβ aggregate growth and produced shorter and fewer fibrils (Du and Murphy, 2010). With CG3, lightly stained spherical deposits were also observed.

The inventors propose the following hypothesis to reconcile all of the data on CG3's effect on Aβ aggregation. Previously, they observed that mTTR greatly suppresses Aβ aggregation both by suppressing fibril initiation and by arresting fibril growth, as measured by dynamic light scattering, NTA, ThT, and TEM (De and Murphy, 2010; Yang et al., 2013). Binding of G16 to Aβ, in contrast, causes an increase in aggregation, a modest reduction in ThT fluorescence, and a general shift in morphology of aggregates from fibrillar to clustered or amorphous (Cho et al., 2014). The inventors hypothesize that CG3 more closely resembles the mode of action of mTTR, where it inhibits Aβ fibrillar growth by preferentially binding to Aβ oligomers. The inventors further hypothesize that, unlike mTTR, CG3 has a strong propensity to self-associate, and therefore some of CG3-bound Aβ might collect into large loose clusters.

Effect of Peptides on Aβ Toxicity.

The inventors tested whether TTR-derived peptides were effective at preventing Aβ toxicity, using primary mouse neuronal cultures and the MTS assay. The Aβ preparation alone was very toxic, with only ~35% cell survival (FIGS. 10A-D). None of the peptides by themselves had any effect on neuronal viability (data not shown). Consistent with previous observations, mTTR conferred complete protection from Aβ-mediated toxicity at substoichiometric concentrations (0.8 μM, FIG. 10A). G16 conferred a small but significant protection at the highest dose tested (FIG. 10B). CG3 was much more effective than G16, showing significant protection at 10 μM and greater recovery of cell viability at higher doses (FIGS. 10C-D). At 10 μM, CG2, LG3 and GF had no protective effect (FIG. 10D). GF did show modest protection at the highest dose (40 μM) tested (data not shown).

Relationship Between Structure, Binding, Aggregation, and Toxicity Inhibition.

Building on prior identification of the Aβ binding site domain in TTR (Du et al., 2012), the inventors synthesized several conformationally constrained peptides, and tested them for binding to Aβ, interference with Aβ aggregation, and inhibition of Aβ toxicity. Despite containing all the previously identified required residues for linear sequences to bind Aβ, neither LG2 nor CG2 bound Aβ, nor did they affect Aβ aggregation or inhibit Aβ toxicity. This was an unexpected result, and the inventors speculate that lack of binding is due to either steric restriction (particularly to Thr106 near the hairpin) or to unwanted rearrangement to a non-native-like conformation. The longer LG3, built on the hairpin template, bound to Aβ, but had only modest effects on aggregation and was ineffective as a toxicity inhibitor. Cyclization to CG3 greatly enhanced the effect on Aβ aggregation and toxicity, presumably due to the additional conformational rigidity afforded. As a structural as well as sequence mimic of TTR, CG3 was much more effective than G16 at arresting Aβ aggregation and inhibiting toxicity.

Presumably because of its structural mimicry, CG3's effect on Aβ aggregation is overall more like mTTR than is G16. CG3 effectively suppressed formation of ThT-positive species, much like mTTR, and with both mTTR and CG3 the inventors observed fewer and much shorter Aβ fibrils by TEM. This is in counterdistinction to G16, which delayed but did not prevent the formation of ThT-positive Aβ aggregates, and caused morphological changes in the appearance of Aβ aggregates but did not shorten fibrils. CG3 differs from mTTR, though, when interaction with Aβ is probed with light scattering-techniques that are particularly sensitive to large particles. Specifically, CG3, like G16 and unlike TTR or mTTR, facilitates the formation and rapid growth of a few, very large, Aβ aggregates. However, both CG3 and G16 reduce the fraction of Aβ aggregates that can be removed by filtration or sedimentation. These results may seem at first contradictory, but can be explained once it is recognized that dynamic light scattering reports on the size of aggregates whereas the filtration/sedimentation assays report on the mass fraction of insoluble/filterable aggregates. Taken together, the inventors interpret the data as follows: CG3's primary mechanism of interaction with Aβ is similar to mTTR, in that it inhibits formation of Aβ aggregates and arrests growth of those fibrils that do form. However, in a secondary mechanism of interaction, CG3 causes clustering of some Aβ aggregates, presumably due to CG3's propensity to self-associate.

Compositional Variants.

To expand the scope of the cyclic peptides, we successfully synthesized SEQ ID NOS: 16, 17, and 18. The molecular weight for each peptide was confirmed by MALDI-ToF mass spectrometry and the measured molecular weights are 2437.36 (SEQ ID NO: 16, theoretical 2437.84), 2480.39 (SEQ ID NO: 17, theoretical 2480.91) and 2397.22 (SEQ ID NO: 18, theoretical 2397.75). In reverse phase C18 HPLC purification process, the elution time for Seq 16, 17, and 18 are 15.5 minute, 14.3 minute, and 12.7 minute, respectively. The elution time for SEQ ID NO: 16 and SEQ ID NO: 1 are similar, but the other two mutations lead to more hydrophilic peptides, as expected and as indicated by the shorter elution times. CD spectra were taken of SEQ ID NOS: 16, 17, and 18, and compared to SEQ ID NO: 1 (data not shown). Beta-sheet content was increased in SEQ ID NO: 16 and SEQ ID NO: 17, making these preferred embodiments. Using the PICUP crosslinking technique, the extent of self-association was measured. SEQ ID NO: 17 demonstrated significantly less self-association than SEQ ID NO: 1 (data not shown). Together, these experiments demonstrate that compositional variations can be used to tune the physicochemical properties of the cyclic peptide.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods, and in the steps or in the sequence of steps of the methods described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VII. REFERENCES

The following references, to the extent that they provide exemplary procedural or other details supplementary to those set forth herein, are specifically incorporated herein by reference.

Alsina, et al., *Lett. Pept. Sci.* 6:243-245, 1999.
Anthis and Clore, *Protein Science* 22:851-858, 2013.
Bean, et al., *J. Am. Chem. Soc.* 114:5328-5334, 1992.
Bitan et al., *Proc. Natl. Acad. Sci. U.S.A.* 100:330-335, 2003.
Bodanszky et al., *J. Antibiot.*, 29(5):549-53, 1976.
Buxbaum et al., *Proc. Natl. Acad. Sci. U.S.A.* 105:2681-2686, 2008.
Cho et al., *ACS Chem. Neurosci.* 5:542-551, 2014.
Craik et al., *Chem. Biol. Drug. Des.* 81:136-147, 2013.
Du and Murphy, *Biochemistry* 49:8726-8289, 2010.
Du et al., *Protein Eng. Des. Sel.* 25:337-345, 2012.
Eichler, *Curr. Opin. Chem. Biol.* 12:707-713, 2008.
Favre et al., *J. Am. Chem. Soc.* 121:2679-2685, 1999.
Gellman, *Curr. Opin. Chem. Biol.* 2:717-725 1998.
Gibbs et al., *Nat. Struct. Mol. Biol.* 5:284-288, 1998.
Giunta et al., *Clin. Biochem.* 38:1112-1119, 2005.
Haass and Selkoe, *Nat. Rev. Mol. Cell. Biol.* 8:101-112, 2007.

Karran et al., *Nat. Rev. Drug Discovery* 10:698-712, 2011.
Klaassen, In: *The Pharmacological Basis of Therapeutics*, Goodman and Gilman, Eds., Pergamon Press, 8$^{th}$ Ed., 1990.
Lesné et al., *Nature.* 440:352-357, 2006.
Li, et al., *J. Neurosci.* 31:12483-12490, 2011.
Lu and Murphy, *J. Pept. Sci.,* 2014
Merrifield, *J. Am. Chem. Soc.,* 85(14):2149-2154, 1963.
Milroy et al., *Chem. Rev.* 114:4695-4748, 2014.
Peptide Synthesis, 1985.
Physicians Desk Reference.
Protective Groups in Organic Chemistry, 1973.
Remington's Pharmaceutical Sciences, 15$^{th}$ ed., pages 1035-1038 and 1570-1580, Mack Publishing Company, Easton, Pa., 1980.
Robinson, *Acc. Chem. Res.* 41:1278-1288, 2008.
Roychaudhuri et al., *J. Biol. Chem.* 284:4749-4753, 2009.
Solid Phase Peptide Synthelia, 1984.
Soto et al., *Nat Med* 4, 822-826, 1998.
Stein and Johnson, *J. Neurosci.* 22:7380-7388, 2002.
Stein et al., *J. Neurosci.* 24:7707-7717, 2004.
Syud, et al., *J. Am. Chem. Soc.* 123:8667-8677, 2001.
Takahashi and Mihara, *Acc. Chem. Res.* 41:1309-1318, 2008.
Taylor et al., *Biochemistry-Us* 49:3261-3272, 2010.
The Merck Index, 11th Edition.
Tjernberg et al., *J. Biol. Chem.* 271:8545-8548, 1996.
U.S. Pat. No. 4,554,101
Walters and Murphy, *J. Mol. Biol.* 412:505-519, 2011
Yang, et al., *Biochemistry* 52:2849-2861, 2013

---

What is claimed is:

1. A cyclized peptide comprising the sequence SKVVTPXRYXIAALLXPYXXXQ (SEQ ID NO: 2), wherein X represents the same amino acid or a conservative amino acid substitution of the corresponding position in the sequence SKVVTPPRYTIAALLSPYSYSQ (SEQ ID NO: 1).

2. The cyclized peptide of claim 1, wherein the P residue at position 6 of SEQ ID NO: 1 or SEQ ID NO: 2 is a D-amino acid.

3. A composition of matter comprising (i) a cyclized peptide comprising the sequence SKVVTPXRYXIAALLXPYXXXQ (SEQ ID NO: 2), wherein X represents the same amino acid or a conservative amino acid substitution of the corresponding position in the sequence SKVVTPPRYTIAALLSPYSYSQ (SEQ ID NO: 1), wherein said terminal S or T and Q residues are covalently bonded to each other, and (ii) a pharmaceutical buffer, carrier, diluent or excipient.

4. The composition of matter of claim 3, wherein the P residue at position 6 of SEQ ID NO: 1 or SEQ ID NO: 2 is a D-amino acid.

5. The composition of matter of claim 3, wherein said composition is formulated for delivery via injection or inhalation.

6. A method of producing a cyclized peptide comprising the sequence SKVVTPXRYXIAALLXPYXXXQ (SEQ ID NO: 2), wherein X represents the same amino acid or a conservative amino acid substitution of the corresponding position in the sequence SKVVTPPRYTIAALLSPYSYSQ (SEQ ID NO: 1), wherein said terminal S or T and Q residues are covalently bonded to each other, said method comprising the steps of:

(a) coupling Fmoc-D-Glu-ODmab to a resin through the unprotected side chain;
(b) assembling the peptide backbone using standard solid-phase synthesis;
(c) deprotecting the Dmab protecting group;
(d) performing on-resin cyclization with benzotriazol-1-yl-N-oxy-tris(pyrrolidino)-phosphonium hexafluorophosphate; and
(e) cleaving peptide from resin using a cleavage cocktail.

7. The method of claim 6, wherein said resin is Fmoc-PAL-PEG-PS resin.

8. The method of claim 6, wherein deprotecting comprises treatment with 2% hydrazine monohydrate in dimethylformamide followed by treatment with 10% diisopropylethylamine in dimethylformamide.

9. The method of claim 6, wherein step (d) comprises treatment for at least 12 hours.

10. The method of claim 6, wherein step (e) comprises use of a cleavage cocktail comprising of 81.5% trifluoroacetic acid, 5% thioanisole, 5% phenol, 5% water and 2.5% ethanedithiol, optionally for 4 hours.

11. A method of protecting neurons from Aβ toxicity in a subject comprising administering to said subject a cyclized peptide comprising the sequence SKVVTPXRYXIAALLXPYXXXQ (SEQ ID NO: 2), wherein X represents the same amino acid or a conservative amino acid substitution of the corresponding position in the sequence SKVVTPPRYTIAALLSPYSYSQ (SEQ ID NO: 1).

12. The method of claim 11, wherein said subject is a human.

13. The method of claim 11, wherein said subject is a non-human mammal.

14. The method of claim 11, wherein the P residue at position 6 of SEQ ID NO: 1 or SEQ ID NO: 2 is a D-amino acid.

15. The method of claim 11, wherein said cyclized peptide is administered via injection.

16. The method of claim 11, wherein said cyclized peptide is administered via nasal inhalation.

17. The method of claim 11, wherein said cyclized peptide is administered orally.

18. The method of claim 11, wherein said cyclized peptide is administered multiple times.

19. The method of claim 11, wherein said cyclized peptide is administered daily.

20. The method of claim 11, further comprising administering to said subject a second agent that abrogates Aβ toxicity.

21. The method of claim 11, wherein said second agent that abrogates Aβ toxicity is a γ- or β-secretase inhibitor, or an inhibitor of $A\beta_{42}$ levels.

22. The method of claim 11, further comprising administering to said subject a cognition improving agent.

23. The method of claim 11, wherein said subject is diagnosed as having Alzheimer's Disease.

24. The method of claim 11, wherein said subject is suspected as having Alzheimer's Disease.

25. The method of claim 11, wherein said subject is genetically at risk of developing Alzheimer's Disease.

* * * * *

SEQUENCE LISTING

```
<160> NUMBER OF SEQ ID NOS: 23

<210> SEQ ID NO 1
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 1

Ser Lys Val Val Thr Pro Pro Arg Tyr Thr Ile Ala Ala Leu Leu Ser
1               5                   10                  15

Pro Tyr Ser Tyr Ser Gln
            20

<210> SEQ ID NO 2
<211> LENGTH: 22
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (19)..(21)
<223> OTHER INFORMATION: Xaa can be any naturally occurring amino acid

<400> SEQUENCE: 2

Ser Lys Val Val Thr Pro Xaa Arg Tyr Xaa Ile Ala Ala Leu Leu Xaa
1               5                   10                  15

Pro Tyr Xaa Xaa Xaa Gln
            20

<210> SEQ ID NO 3
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 3
```

```
Ser Lys Val Val Thr Pro Pro Arg Tyr Ala Ile Ala Ala Leu Leu Ser
1               5                   10                  15

Pro Tyr Ser Tyr Ser Gln
            20

<210> SEQ ID NO 4
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 4

Ser Lys Val Val Thr Pro Pro Arg Tyr Thr Ile Ala Ala Leu Leu Ala
1               5                   10                  15

Pro Tyr Ser Tyr Ser Gln
            20

<210> SEQ ID NO 5
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 5

Ser Lys Val Val Thr Pro Pro Arg Tyr Thr Ile Ala Ala Leu Leu Ser
1               5                   10                  15

Pro Tyr Ala Tyr Ser Gln
            20

<210> SEQ ID NO 6
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 6

Ser Lys Val Val Thr Pro Pro Arg Tyr Thr Ile Ala Ala Leu Leu Ser
1               5                   10                  15

Pro Tyr Ser Tyr Ala Gln
            20

<210> SEQ ID NO 7
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 7

Ser Lys Val Val Thr Pro Pro Arg Tyr Thr Ile Ala Ala Leu Leu Ser
1               5                   10                  15

Pro Tyr Ser Trp Ser Gln
            20

<210> SEQ ID NO 8
<211> LENGTH: 22
<212> TYPE: PRT
<213> ORGANISM: Artificial Sequence
<220> FEATURE:
<223> OTHER INFORMATION: Synthetic Peptide
```

```
<400> SEQUENCE: 8

Ser Lys Val Val Thr Pro Gly Arg Tyr Thr Ile Ala Ala Leu Leu Ser
1               5                   10                  15

Pro Tyr Ser Tyr Ser Gln
            20

<210> SEQ ID NO 9
<211> LENGTH: 22
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: D-amino acid

<400> SEQUENCE: 9

Ser Lys Val Val Thr Pro Gly Arg Tyr Thr Ile Ala Ala Leu Leu Ser
1               5                   10                  15

Pro Tyr Ser Tyr Ser Gln
            20

<210> SEQ ID NO 10
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 10

Pro Arg Arg Tyr Thr Ile Ala Ala Leu Leu Ser Pro Tyr Ser Trp Ser
1               5                   10                  15

<210> SEQ ID NO 11
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 11

Pro Arg Arg Tyr Thr Ile Ala Ala Leu Leu Ser Pro Tyr Ser Trp Ser
1               5                   10                  15

Asp Tyr Lys Asp Asp Asp Asp Lys
            20

<210> SEQ ID NO 12
<211> LENGTH: 18
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: D-amino acid

<400> SEQUENCE: 12

Ser Lys Val Pro Pro Thr Ile Ala Ala Leu Leu Ser Pro Tyr Ser Tyr
1               5                   10                  15

Ser Gln

<210> SEQ ID NO 13
<211> LENGTH: 22
```

```
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: D-amino acid

<400> SEQUENCE: 13

Ser Lys Val Val Thr Pro Pro Arg Tyr Thr Ile Ala Ala Leu Leu Ser
1               5                   10                  15

Pro Tyr Ser Tyr Ser Gln
            20

<210> SEQ ID NO 14
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 14

Thr Ile Ala Ala Leu Leu Ser Pro Tyr Ser Tyr Ser
1               5                   10

<210> SEQ ID NO 15
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 15

Pro Arg Arg Tyr Thr Ile Ala Ala Leu Leu Ser Pro Tyr Ser Trp Ser
1               5                   10                  15

Thr Thr Ala Val Val Thr Asn Pro
            20

<210> SEQ ID NO 16
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 16

Thr Lys Val Val Thr Pro Pro Arg Tyr Thr Ile Ala Ala Leu Leu Ser
1               5                   10                  15

Pro Tyr Ser Tyr Ser Gln
            20

<210> SEQ ID NO 17
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 17

Ser Lys Val Val Thr Pro Pro Arg Tyr Thr Ile Ala Lys Leu Leu Ser
1               5                   10                  15

Pro Tyr Ser Tyr Ser Gln
            20
```

```
<210> SEQ ID NO 18
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 18

Ser Lys Val Val Thr Pro Pro Arg Tyr Thr Ile Ala Ala Leu Ser Ser
1               5                   10                  15

Pro Tyr Ser Tyr Ser Gln
            20

<210> SEQ ID NO 19
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 19

Thr Lys Val Val Thr Pro Pro Arg Tyr Thr Ile Ala Lys Leu Leu Ser
1               5                   10                  15

Pro Tyr Ser Tyr Ser Gln
            20

<210> SEQ ID NO 20
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 20

Thr Lys Val Val Thr Pro Pro Arg Tyr Thr Ile Ala Ala Leu Ser Ser
1               5                   10                  15

Pro Tyr Ser Tyr Ser Gln
            20

<210> SEQ ID NO 21
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 21

Thr Lys Val Val Thr Pro Pro Arg Tyr Thr Ile Ala Lys Leu Ser Ser
1               5                   10                  15

Pro Tyr Ser Tyr Ser Gln
            20

<210> SEQ ID NO 22
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 22

Ser Lys Val Val Thr Pro Pro Arg Tyr Thr Ile Ala Lys Leu Ser Ser
1               5                   10                  15

Pro Tyr Ser Tyr Ser Gln
            20
```

-continued

```
<210> SEQ ID NO 23
<211> LENGTH: 7
<212> TYPE: PRT
<213> ORGANISM: Artificial Sequence
<220> FEATURE:
<223> OTHER INFORMATION: Synthetic peptide

<400> SEQUENCE: 23

Lys Leu Val Phe Phe Ala Glu
1               5
```